United States Patent [19]
Nakamura et al.

[11] Patent Number: 5,925,882
[45] Date of Patent: Jul. 20, 1999

[54] SCINTILLATION CAMERA AND SENSOR FOR USE THEREIN

[75] Inventors: Nobuyuki Nakamura, Yaita; Toshikatsu Ruike; Tsutomu Yamakawa, both of Tochigi-ken, all of Japan

[73] Assignee: Kabushiki Kaisha Toshiba, Kawasaki, Japan

[21] Appl. No.: 08/845,239

[22] Filed: Apr. 21, 1997

Related U.S. Application Data

[63] Continuation of application No. 08/142,050, Oct. 28, 1993, Pat. No. 5,625,191.

[30] Foreign Application Priority Data

| Oct. 28, 1992 | [JP] | Japan | 4-290511 |
| Feb. 2, 1993 | [JP] | Japan | 5-015705 |
| Mar. 25, 1993 | [JP] | Japan | 5-066432 |
| May 7, 1993 | [JP] | Japan | 5-107043 |

[51] Int. Cl.$^6$ .................................................. G01T 1/166
[52] U.S. Cl. .............................. 250/363.05; 250/363.02; 250/363.04; 250/363.08
[58] Field of Search ................... 250/363.02, 363.04, 250/363.05, 363.08

[56] References Cited

U.S. PATENT DOCUMENTS

| 4,445,035 | 4/1984 | Ueyama | 250/363.04 |
| 4,593,189 | 6/1986 | Stoub | 250/363.04 X |
| 5,319,205 | 6/1994 | Kline et al. | 250/363.04 |
| 5,376,796 | 12/1994 | Chan et al. | 250/363.04 |
| 5,486,700 | 1/1996 | Silberklang et al. | 250/363.04 |

FOREIGN PATENT DOCUMENTS

| 59-63583 | 4/1984 | Japan | 250/363.04 |
| 59-79879 | 5/1984 | Japan | 250/363.04 |

*Primary Examiner*—Constantine Hannaher
*Attorney, Agent, or Firm*—Oblon, Spivak, McClelland, Maier & Neustadt, P.C.

[57] ABSTRACT

A scintillation camera having a detector with a surface and designed to form a tomographic image of a subject from radiation emitted from radioisotope administered to the subject and detected by the detector. The camera comprises a data acquiring device for acquiring data required to reconstruct a tomographic image of the subject, and a detector holder for holding the detector at a predetermined distance from the body surface of the subject while the data acquiring device is acquiring the data. The detector holder includes a sensor located between the subject and the detection surface of the detector, a sensor control circuit for controlling the sensor and detecting ON/OFF state of the sensor, and a detector moving device for moving the detector toward and away from the subject in accordance with the ON/OFF state detected by the sensor control circuit.

23 Claims, 24 Drawing Sheets

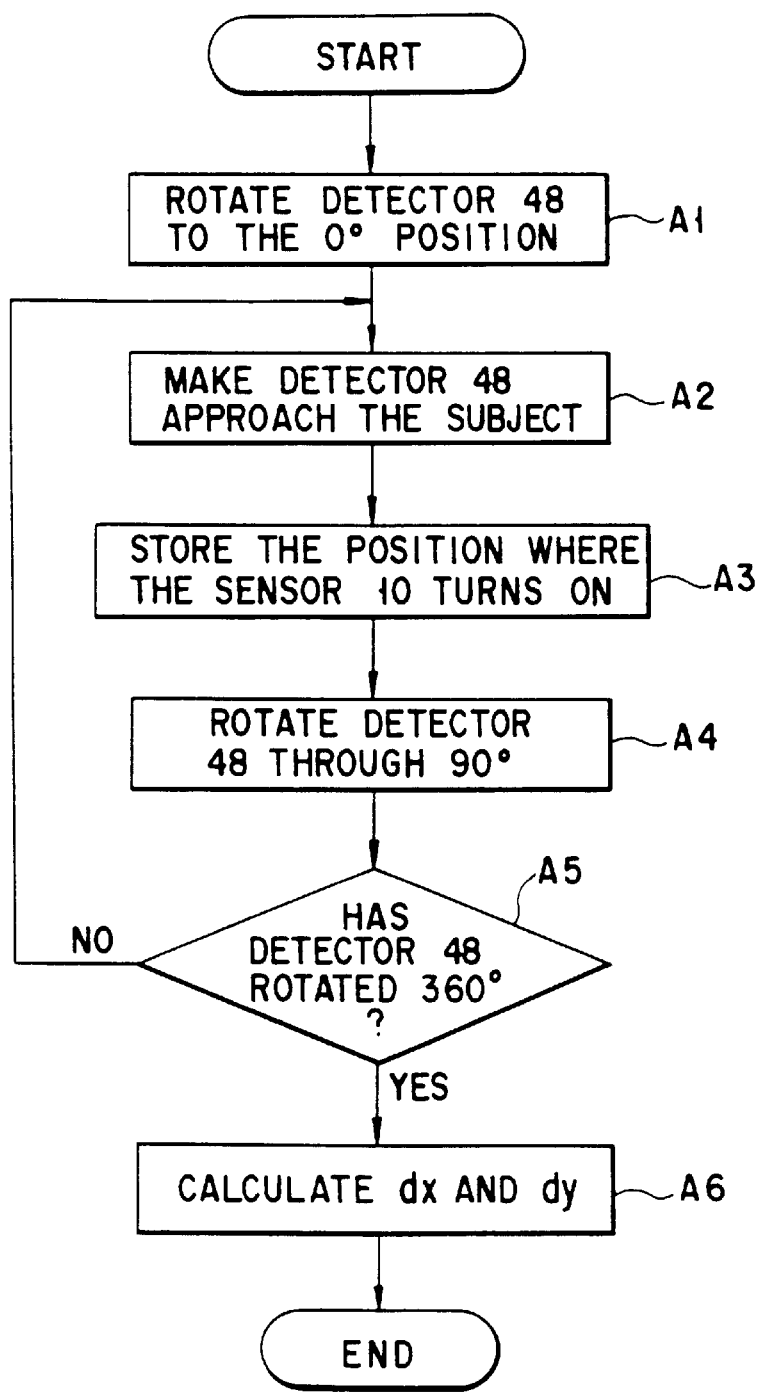
F I G. 15

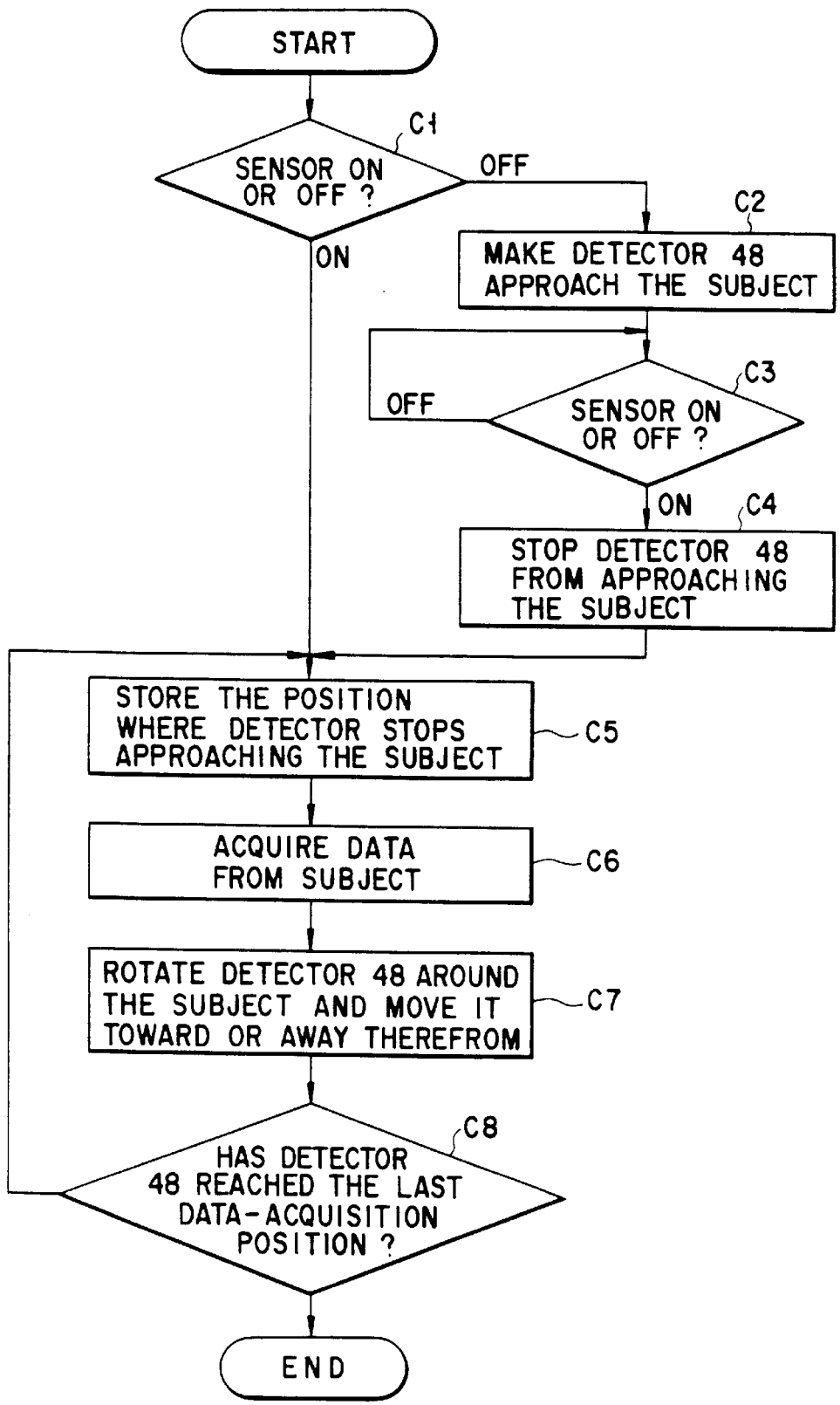
F I G. 19

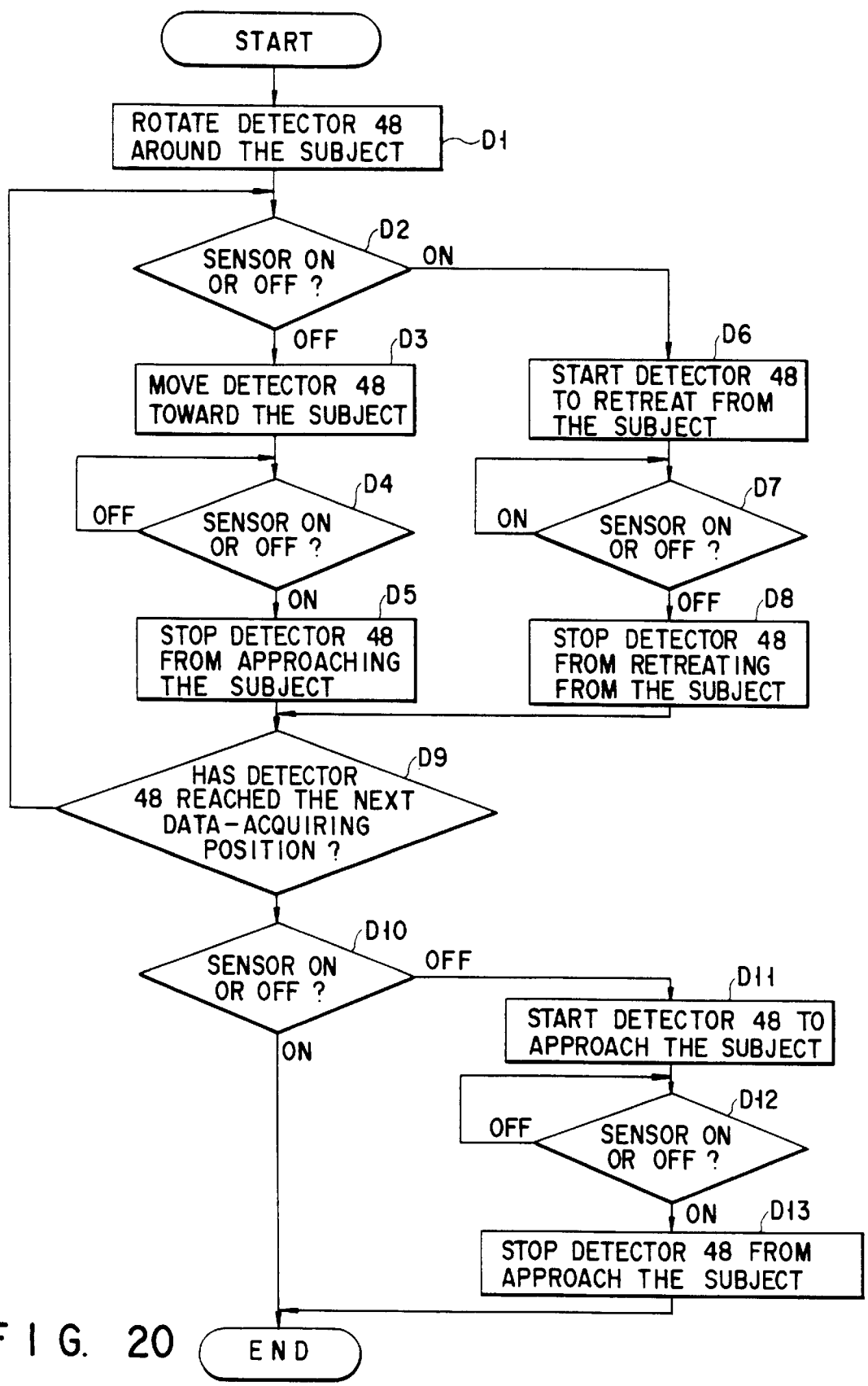
F I G. 20

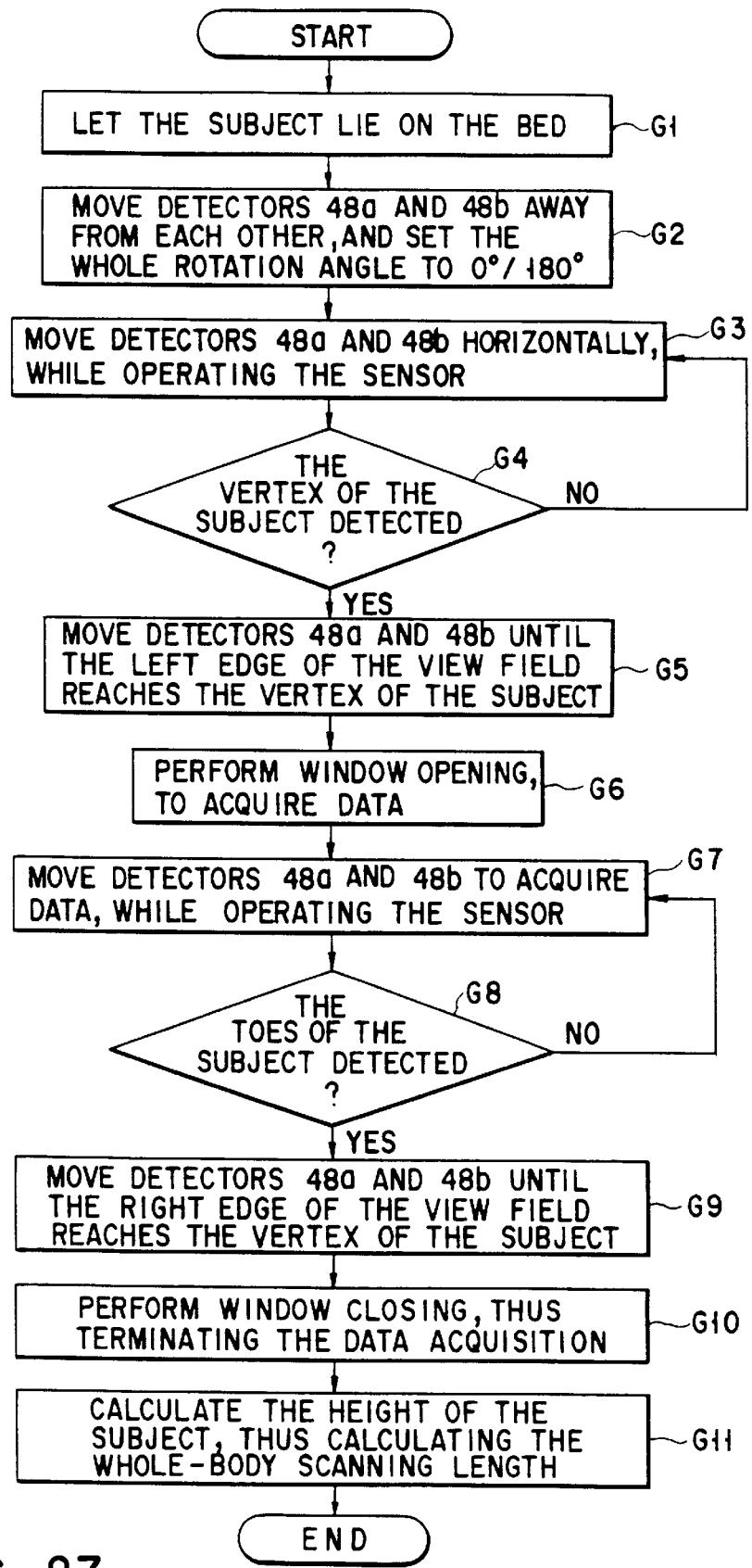
F I G. 27

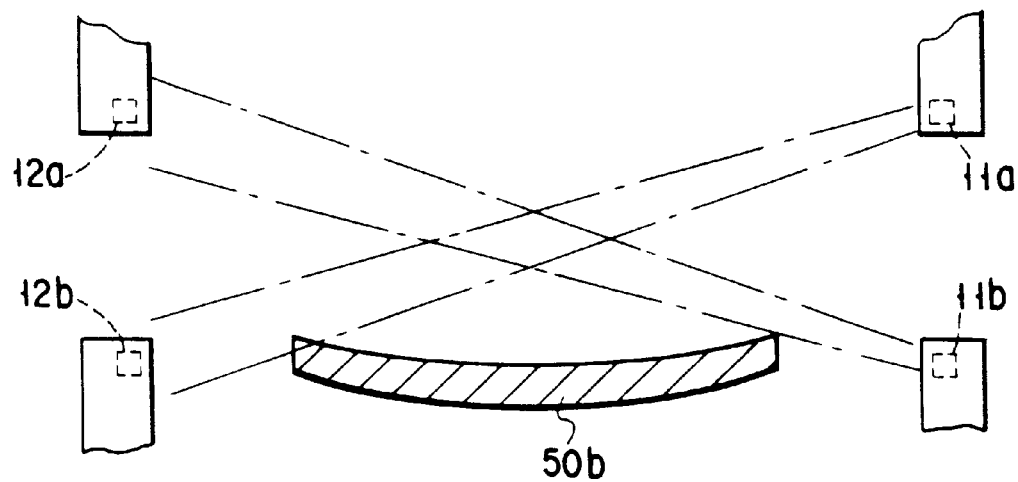
F I G. 28A
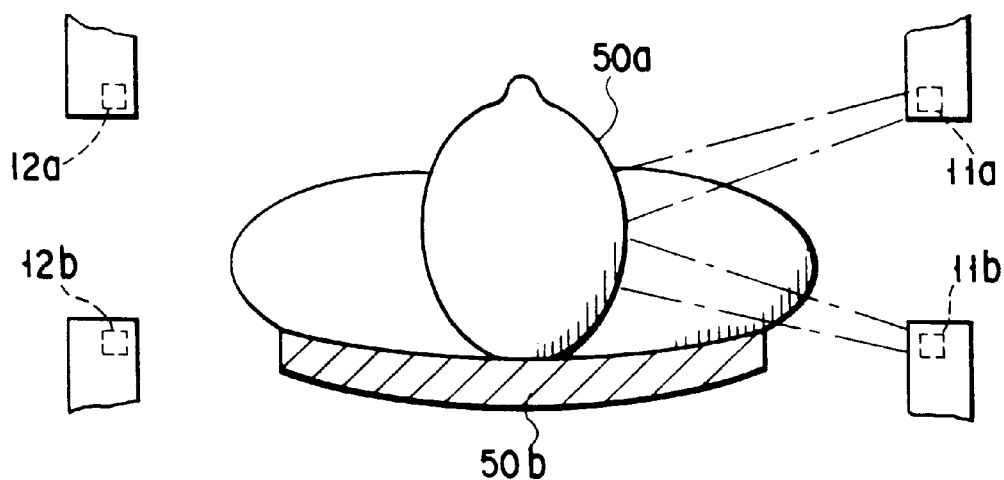
F I G. 28B

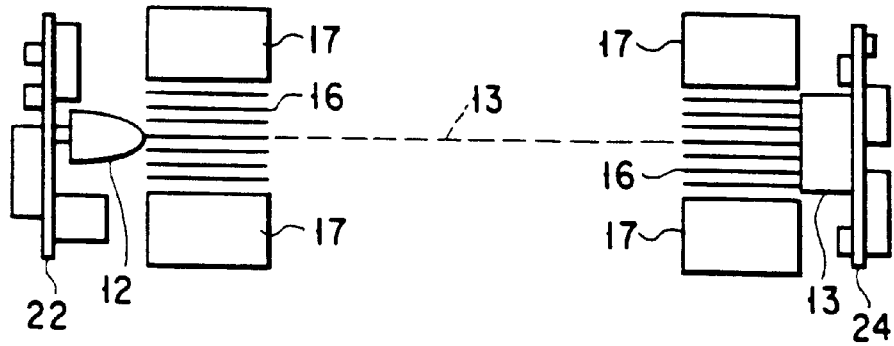
F I G. 29
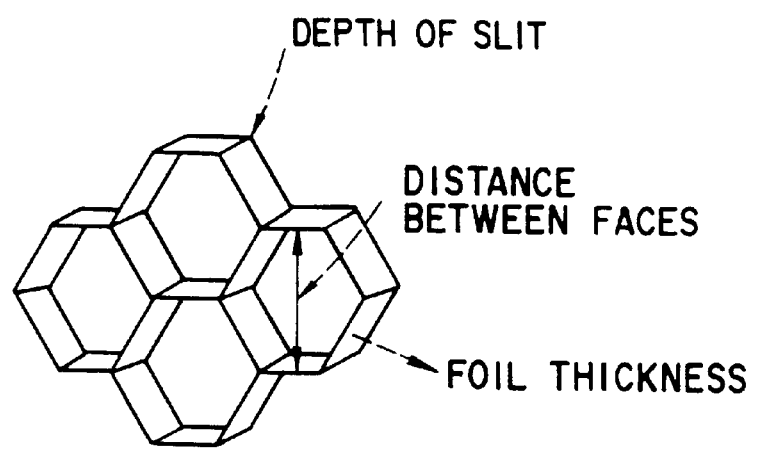
F I G. 30

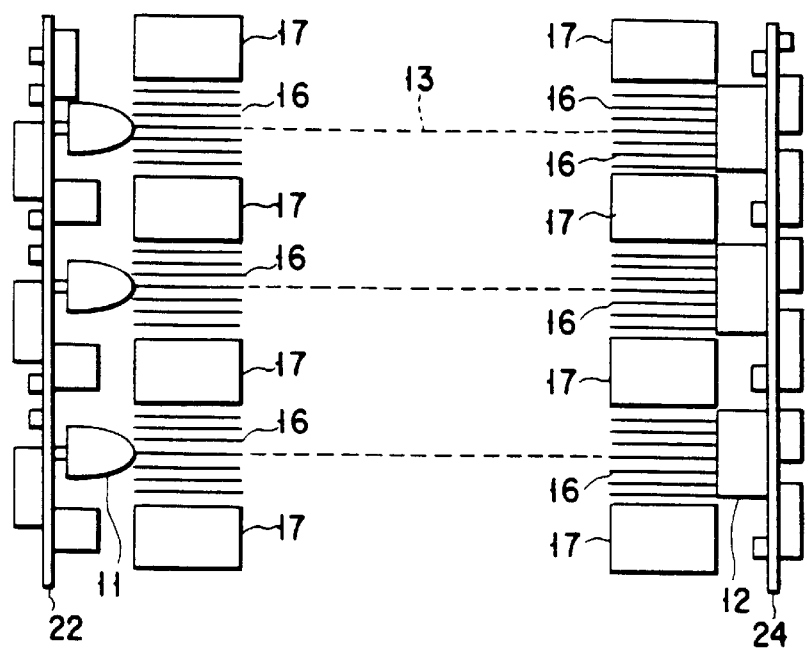
F I G. 34
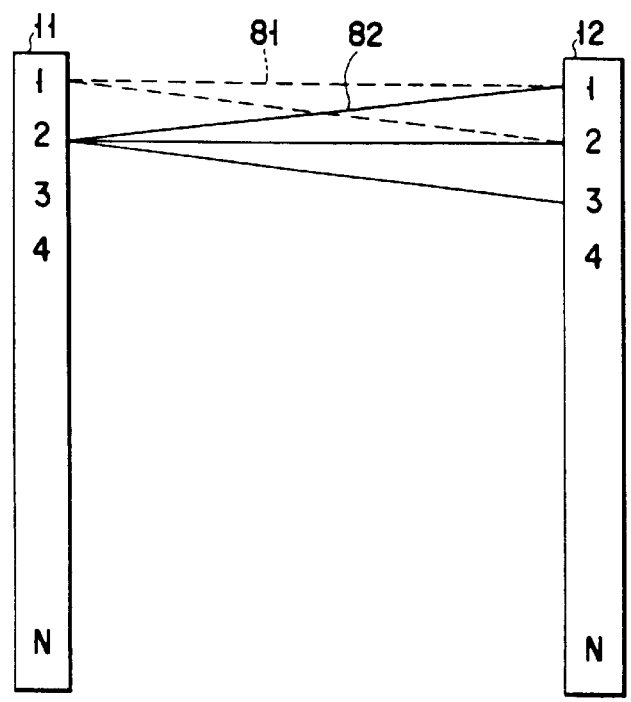
F I G. 35

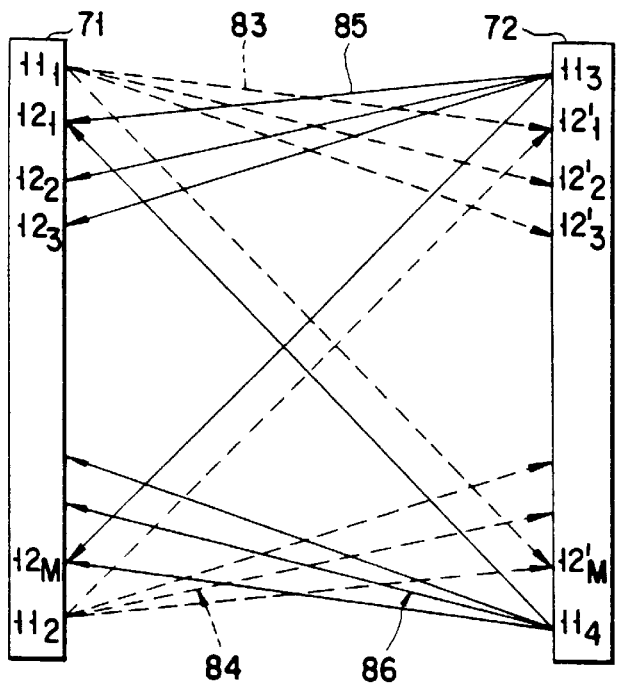
F I G. 36
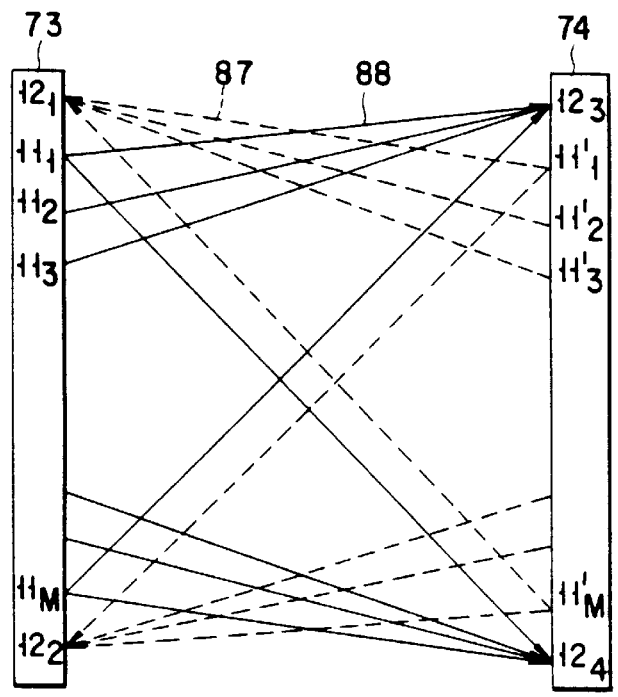
F I G. 37

SCINTILLATION CAMERA AND SENSOR FOR USE THEREIN

This is a Continuation, of application Ser. No. 08/142,050 filed on Oct. 28, 1993, now U.S. Pat. No. 5,625,191

BACKGROUND OF THE INVENTION

1. Field of the Invention

The present invention relates to a scintillation camera, more particularly to the scanning of a subject by means of a detector incorporated in the scintillation camera, and to a non-contact type sensor for use in a nuclear medicine diagnostic apparatus or in an X-ray diagnostic apparatus.

2. Description of the Related Art

A scintillation camera is used to form a functional image of a living subject while a detector is scanning the subject and detecting the gamma-rays emitted from the radioisotope labeled with a specific medicine administered to the subject.

The camera serves to determine, from the gamma-rays detected, the distribution of the radioisotope within the subject, in order to thereby visualize the shape and functional condition of an organ, the presence or absence of a lesion, and metabolic function of the subject. Although it has a low resolution and involves radiation exposure of the subject, it is used in specific fields such as the early detection of a brain ischemia section and estimation of the viability of myocardial cells. The scintillation camera serves as an apparatus which assists an X-ray computed tomography apparatus.

A conventional scintillation camera is operated to scan to obtain a SPECT (Single Photon Emission Computed Tomographic) image of a subject by one of the following two alternative methods.

The first method, generally known as "4-point determination method," serves to input four points before the detector of the camera is moved around a subject to scan the subject. Of these points, two are on a major axis extending in the width direction of the subject, and the other two are on a minor axis extending in the thickness direction of the subject. That is, an appropriate distance from the center of rotation along the turning radius is input every time the detector is rotated by 90°, thereby calculating an arc for each quadrant. The detector is thereby moved in an elliptical orbit passing the four points.

The second method is to rotate the detector once around the subject in an elliptical orbit, before the acquisition of data from the subject, thereby obtaining data representing the elliptical orbit. Then, the detector is moved around the subject along the elliptical orbit represented by the data, to scan the subject.

In the first method, data items representing the four points must be input to define an elliptical orbit, prior to the scanning of the subject. In the second method, the detector must be moved once around the subject in an elliptical orbit to acquire the data representing this orbit, prior to the scanning of the subject. In either method it is necessary to set an orbit for the detector before the acquisition of data from the subject. Furthermore, the subject may move after the orbit has been set, making it necessary to adjust the orbit. However, the orbit can hardly be adjusted once it has been thus set or once the data acquisition has been started.

Particularly, in the 4-point determination method, the orbit for the detector is an elliptical one which has not been set on the basis of the outline of a transverse section of the subject. The orbit is not an ideal orbit which should preferably closely surround the subject.

As indicated above, the conventional scintillation camera cannot be used before an orbit is set for the detector or the data representing such an orbit is input. The subject may move, making it necessary to adjust the orbit. However, it is difficult to adjust the orbit once the orbit has been set or once the data acquisition has been initiated. Further, in the 4-point determination method it is impossible to set an ideal orbit closely surrounding the subject.

A scintillation camera of so-called "whole body type," is known, which scans a subject while its detector is moving along the body axis of the subject. The conventional whole body-type scintillation camera is operated to scan a subject by one of the following three alternative methods.

In the first method, as shown in FIG. 1A, the detector 48 is located at a position which has been determined based on the highest point of the ridge line showing the lateral section of the subject 50 lying on the bed (hereinafter, referred to as only a subject for simplicity in some cases). Then, the detector 48 is moved along the body axis of the subject 50, while maintained at that position, to thereby scan the whole body of the subject 50.

In the second method, as shown in FIG. 1B, the detector 48 is moved along the ridge line of the subject 50, prior to the scanning of the subject 50, thereby obtaining data representing the curved path of the detector 48. Then, the detector 48 is automatically moved along the curved path represented by the data thus obtained, to thereby scan the whole body of the subject 50.

In the third method, the detector is located at a scanning start position, a scanning length, or a scanning end position, is determined on the basis of the height of a subject and input, and the detector is moved from the scanning start position to the scanning end position. While being so moved, the detector acquires whole-body data from the subject.

The three methods have problems, however.

The first method is problematic in two respects. First, it takes many times to determine a proper position for the detector 48. Second, the detector 48 is positioned too far a distance away from the subject 50, except for a moment it is located close to the highest point on the ridge line. The resolution of the scintillation camera is therefore decreased.

The second method is problematic in two respects, too. First, it takes too much time to obtain the data showing the curving path of the detector 48. Second, data acquisition from the subject 50 is interrupted when the subject 50 moves, inadvertently touching the detector 48, as often happens, while the detector 48 is moving along the curving path.

The third method is problematic in two respects, too. First, an operator must take pains to locate the detector at a scanning start position where the head or toes of the subject is completely within the view field of the detector, while looking at the image picked up by the detector. Inevitably it takes a long time to locate the detector at a desirable scanning start position. Second, it is necessary for the operator to determine the scanning length, or the scanning end position, on the basis the height of the subject, and to input the scanning length. To determine and input the scanning length is also time-consuming.

Scintillation cameras are used, each in combination with one sensor.

The sensor comprises a plurality of light-emitting elements and a plurality of light-receiving elements, which are arranged in the same plane. The light-receiving elements oppose the light-emitting elements, respectively, spaced apart therefrom by a predetermined distance. The sensor is designed for industrial use. When all light-receiving elements receive light from the associated light-emitting elements, it is determined that no object lies between the light-emitting elements on the one hand, and the light-receiving elements on the other hand. When any one of the light-receiving elements does not receive light from the associated light-emitting element, it is determined that an object lies between the light-emitting elements and the light-receiving elements.

FIG. 2 schematically shows a conventional sensor of this type.

As shown in FIG. 2, a plurality of light-emitting elements $11_1$ to $11_N$ and a plurality of the light-receiving elements $12_1$ to $12_N$ are arranged in the same plane. The elements $12_1$ to $12_N$ oppose the light-emitting elements $11_1$ to $11_N$, respectively, spaced apart therefrom by a predetermined distance. Each light-receiving element 12 receives the light emitted from the associated light-emitting element 11. The optical axis extending between each light-emitting element 11 and the associated light-receiving element 12, shown by a broken line, is parallel to the optical axis extending between any other associated elements 11 and 12. When an object 50 exists between the light-emitting elements 11 on the one hand and the light-receiving elements 12 on the other hand, at least one of the light-receiving elements 12 cannot receive the light emitted by the associated light-emitting element 11. Thus, the presence or absence of an object can be determined from the signals output by the light-receiving elements 12. The light-emitting elements 11 and the light-receiving elements 12 are controlled by a sensor controller 20. The controller 20 generates a signal representing the presence or absence of an object. This signal is used for various purposes. The plane in which the elements 11 and 12 are arranged is either horizontal or vertical, in accordance with the purpose for which the sensor is employed.

The sensor for industrial use, shown in FIGS. 3A and 3B, may make errors when a light-reflecting object is located in the vicinity of the light-emitting elements 11 and the light-receiving elements 12.

As shown in FIG. 3A, a light-reflecting flat object may be located near the light-emitting elements 11 and the light-receiving elements 12. In this case, the light emitted from any light-emitting element 11 is reflected or scattered on the reflecting surface of the object and is then applied to the light-receiving element 12 associated with the light-emitting element 11.

As shown in FIG. 3B, the sensor may be located near a light-reflecting wall or floor. In this case, too, the light emitted from any light-emitting element 11 is reflected or scattered on the reflecting surface of the object and is then applied to the light-receiving element 12, associated with the light-emitting element 11.

In either case, the sensor outputs a signal representing the absence of an object, despite the fact that there is an object located between the light-emitting element 11 and the light-receiving element 12.

A sensor of the type shown in FIG. 2 is often used in combination with the medical scintillation camera described above, with its light-emitting elements 11 attached to one end of the camera, and its light-receiving elements 12 secured to the other end of the camera. The scintillation camera, which is a reflector, extends parallel to the optical axis of the sensor. The light reflected from and scattered by the scintillation camera adversely affects the reliability of the sensor. When the sensor makes an error due to the reflected or scattered light, the camera may abut on a subject or may be stopped.

SUMMARY OF THE INVENTION

An object of the present invention is to provide a scintillation camera which can easily acquire data required for reconstructing a tomographic image of a subject, without the necessity of setting an orbit for a detector prior to the acquisition of data, which has an enhanced image resolution, which can effectively acquire data regardless of the subject's body shape, and which can continue to acquire data even if the subject moves during the data acquisition.

In a first aspect of the present invention, there is provided a scintillation camera having a detector with a detector surface and designed to form a tomographic image of a subject from radiation emitted from radioisotope administered to the subject and detected by the detector. The camera comprises: data acquiring means for acquiring data required to reconstruct a tomographic image of the subject; and detector holding means for holding the detector at a predetermined distance from the body surface of the subject while the data acquiring means is acquiring the data.

The scintillation camera is characterized in that the detector holding means includes: a sensor located between the subject and the detection surface of the detector; a sensor control circuit for controlling the sensor and detecting ON/OFF state of the sensor; and detector moving means for moving the detector toward and away from the subject in accordance with the ON/OFF state detected by the sensor control circuit.

As indicated, the detector holding means holds the detector at a predetermined distance from the subject during the data acquisition. Therefore, an orbit in which the detector is to rotate around the subject need not be set prior to the data acquisition, by inputting four points as in the 4-point determination method. Nor is it necessary to input data showing the orbit into the scintillation camera prior to the data acquisition. Hence, the preparation time for data acquisition can be shortened.

Since the detector holding means holds the detector at a predetermined distance from the subject throughout the data acquisition, the data acquisition need not be interrupted at all even if the subject moves while being scanned. For the same reason, the detector rotates in an optimal orbit around the subject, however shaped the subject is.

Moreover, accurate data representing the ridge line of the subject can be recorded from the orbit in which the detector has been rotated around the subject and can be utilized as absorption-correcting data in order to reconstruct a tomographic image of the subject.

In a second aspect of the invention, there is provided a scintillation camera having a detector with a detector surface and designed to obtain a distribution of the radiation emitted from radioisotope administered to the subject and detected by the detector while the detector is being moved relative to the subject along a body axis of the subject. This camera comprises: data acquiring means for acquiring data from the subject; and detector holding means for holding the detector at a predetermined distance from the body surface of the subject while the data acquiring means is acquiring the data.

The scintillation camera is characterized in that the detector holding means includes: a sensor located between the subject and the detection surface of the detector; a sensor control circuit for controlling the sensor and detecting ON/OFF state of the sensor; and detector moving means for moving the detector toward and away from the subject in accordance with the ON/OFF state detected by the sensor control circuit.

With this scintillation camera it is possible to determine whether the detector has approached the subject or retreated therefrom excessively, and to move the detector toward or away from the subject in accordance with the position of the detector, thereby to maintain the detector at a desired distance from the subject throughout the data acquisition. Hence, it is unnecessary to collect data before the data acquisition in order to set an optimal orbit for the detector. Furthermore, the detector can be positioned close to the subject while rotating around the subject even if the subject moves during the data acquisition. This serves to enhance the image resolution of the scintillation camera.

Another object of the present invention is to provide a scintillation camera in which the detector is automatically positioned, moved and stopped.

In a third aspect of the invention, there is provided a scintillation camera having a detector with a detector surface and designed to acquire data from a subject by detecting radiation emitted from radioisotope administered to the subject while the detector is being moved relative to the subject along a body axis of the subject. This scintillation camera comprises: drive means for moving the detector relative to the subject along the body axis of the subject; a sensor connected to the detector, for detecting a position of the subject with respect to the detector and for outputting a signal representing the position of the subject; and control means for controlling the drive means in accordance with the signal output from the sensor.

In the scintillation camera according to the third aspect of the invention, the detector is moved with respect to the subject while the sensor is operating, and the control means causes, based on the signal from the sensor, the driving means to position, move and stop the detector automatically.

Still another object of the invention is to provide a sensor which can reliably detect an object even if a light-reflecting object is located in its neighborhood.

In a fourth aspect of this invention, there is provided a sensor which comprises: a least one light-emitting element for emitting light beam; at least one light-receiving element, opposing the light-emitting element, spaced apart therefrom by a predetermined distance, and located in the same plane as the light-emitting element; and at least one slit unit located between the at least one light-emitting element and the at least one light-receiving element. This sensor is characterized in that the slit unit is a honeycomb slit unit.

The at least one slit unit located between the at least one light-emitting element and the at least one light-receiving element prevents the beam emitted by the at least one light-emitting element from being applied to a reflector, if located nearby, or the light scattered or reflected from such a reflector from reaching the at least one light-receiving element. If the slit unit is a honeycomb slit unit, then it effectively prevents undesired application of a beam to a reflector and undesired application of scattered or reflected light to the at least one light-receiving element.

In a fifth aspect of the present invention, there is provided a sensor which comprises: an array of light-emitting elements for emitting beams; an array of light-receiving elements opposing the light-emitting elements, spaced apart therefrom by a predetermined distance, and arranged in the same plane as the light-emitting elements, for receiving the beams emitted from the light-emitting elements; and means for applying the beam emitted from each light-emitting element sequentially to the light-receiving elements, repeatedly a number of times which is an integral multiple of the number of the light-emitting elements.

In a sixth aspect of the present invention, there is provided a sensor which comprises: two parallel arrays of light-emitting elements; at least two light-receiving elements located at the ends of each of the arrays of light-emitting elements; and means for repeatedly applying the beams sequentially emitted from the light-emitting elements of one of the array to each of at least two light-receiving elements located at the ends of the other array.

The sensors according to the fifth and sixth aspects of this invention are characterized in that it further comprises at least one honeycomb slit unit extending between the two arrays of light-emitting elements.

In the sensor according to the fifth aspect of the invention, the beam emitted from each light-emitting element is sequentially applied to the light-receiving elements, repeatedly a number of times which is an integral multiple of the number of the light-emitting elements. In the sensor according to the sixth aspect of the invention, the beams sequentially emitted from the light-emitting elements of one of the array are repeatedly applied to each of at least two light-receiving elements located at the ends of the other array. In either sensor, not only parallel light beams but also slant, non-parallel light beams are used to detect any object existing between the array of light-emitting and -receiving elements. This helps increase the precision of detecting an object. Use of a honeycomb slit unit, extended between the two arrays of light-emitting and -receiving elements, serves to enhance further the precision of detecting an object.

In a seventh aspect of the invention, there is provided a sensor which has a honeycomb slit unit comprising a compressed honeycomb structure made of a thin plate and coated with dark mat paint, and a frame holding the compressed honeycomb structure.

Since the slit unit comprises a compressed honeycomb structure, the depth, diameter and width of the individual slits can easily be adjusted. As a result, the angle at which a light beam is applied through each slit can be reduced.

In an eighth aspect of this invention, there is provided a sensor which comprises: an array of first to Nth light-emitting elements; an array of first to Nth light-receiving elements opposing the first to Nth light-emitting elements, respectively, spaced apart therefrom by a predetermined distance, and located in the same plane as the first to Nth light-emitting elements; means for repeating a sequence of the steps of:

causing the first light-emitting element to emit beams and the first and second light-receiving elements to receive the beams and generate signals;

causing the second light-emitting element to emit beams and the first, second and third light-receiving elements to receive the beams and generate signals;

causing any Mth light-emitting element (1<M<N) to emit beams and the (M−1)th, Mth and (M+1)th light-receiving elements to receive the beams and generate signals; and causing the Nth light-emitting element to emit beams and the (N−1)th and Nth light-receiving elements to receive the beams and generate signals; and means for recording the beams emitted by the first to Nth light-emitting elements and the signals generated by the first to Nth light-receiving elements, checking the beams and signals against the positions of the first to Nth light-emitting elements and the positions of the first to Nth light-receiving elements, thereby detecting a position of a subject existing between the array of the first to Nth light-emitting elements and the array of the first to Nth light-receiving elements.

In a ninth aspect of this invention, there is provided a sensor which comprises: an array of first to Nth light-emitting elements; an array of first to Nth light-receiving elements opposing the first to Nth light-emitting elements, respectively, spaced apart therefrom by a predetermined distance, and located in the same plane as the first to Nth light-emitting elements; and means for performing two sequences of steps in each cycle of operation when no object exists between the array of first to Nth light-emitting elements and the array of first to Nth light-receiving element.

The first sequence of steps consisting of the steps of:
causing the first light-emitting element to emit beams and the first and second light-receiving elements to receive the beams and generate signals;
causing the second light-emitting element to emit beams and the first, second and third light-receiving elements to receive the beams and generate signals;
causing any Mth light-emitting element (1<M<N) to emit beams and the(M−1)th, Mth and (M+1)th light-receiving elements to receive the beams and generate signals; and
causing the Nth light-emitting element to emit beams and the(N−1)th and Nth light-receiving elements to receive the beams and generate signals.

The second sequence of steps consisting of the steps of:
causing the first light-emitting element not to emit beams and the second and second light-receiving elements to generate signals;
causing the second light-emitting element not to emit beams and the first, second and third light-receiving elements to generate signals;
causing any Mth light-emitting element (1<M<N) not to emit beams and the(M−1)th, Mth and (M+1)th light-receiving elements to generate signals; and
causing the Nth light-emitting element not to emit beams and the(N−1)th and Nth light-receiving elements to generate signals.

With the sensors of the eighth and ninth aspects of the present invention it is possible, by virtue of the above-described sequences of steps performed, to specify the position of any object existing between the two arrays of light-emitting and -receiving elements and to determine whether or not any one of the light-emitting and -receiving elements is out of order.

Any sensor, described above, according to the present invention, has at least one slit unit in front of the array of light-emitting elements or the array of light-receiving elements. Hence, the sensor can detect any object existing between the arrays, not influenced by light scattered or reflected from a reflector, if any, located near the sensor. Since the slit unit comprises a compressed honeycomb structure, the size of the individual slits can easily be adjusted in accordance with the position of the reflector and the those of the light-emitting and -receiving elements.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 15 is a flow chart for explaining the method of locating the body axis;

FIG. 19 is a flow chart for explaining how a scintillation camera, according to the second embodiment of the invention is operated in order to acquire SPECT data from the subject in the stepwise mode;

FIG. 20 is a flow chart explaining, in detail, Step C7 which is one of the steps for operating the scintillation camera according to the second embodiment of the invention;

FIG. 27 is a flow chart for explaining the operation of the scintillation camera shown in FIGS. 26A and 26B;

FIG. 28A is a diagram for explaining how the camera of FIGS. 26A and 26B operates when a subject lies on the bed;

FIG. 28B is a diagram for explaining how the camera of FIGS. 26A and 26B operates when no subject lies on the bed;

FIG. 29 is a diagram showing a first example of the sensor used in t present invention;

FIG. 30 a perspective view of part of the honeycomb structure of one of the identical slit units incorporated in the sensor shown in FIG. 16;

FIG. 34 is a diagram illustrating a third example of the sensor;

FIG. 35 is a diagram showing a fourth example of the sensor;

FIG. 36 is a diagram showing a fifth example of the sensor;

FIG. 37 is a diagram showing a sixth example of the sensor;

DETAILED DESCRIPTION OF THE PREFERRED EMBODIMENTS

Figure 1A:
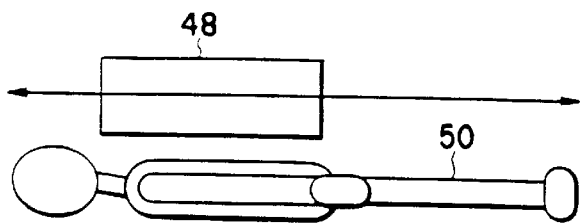
FIGS. 1A and 1B are diagrams showing two alternative orbits along which the detector of a conventional scintillation camera may be moved.
Figure 1B:
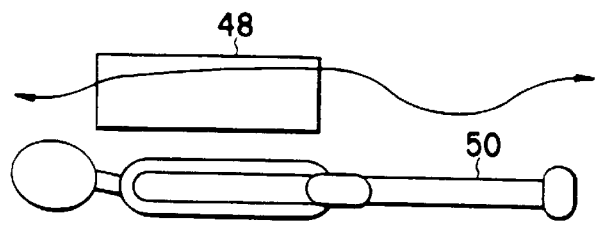
Figure 2:
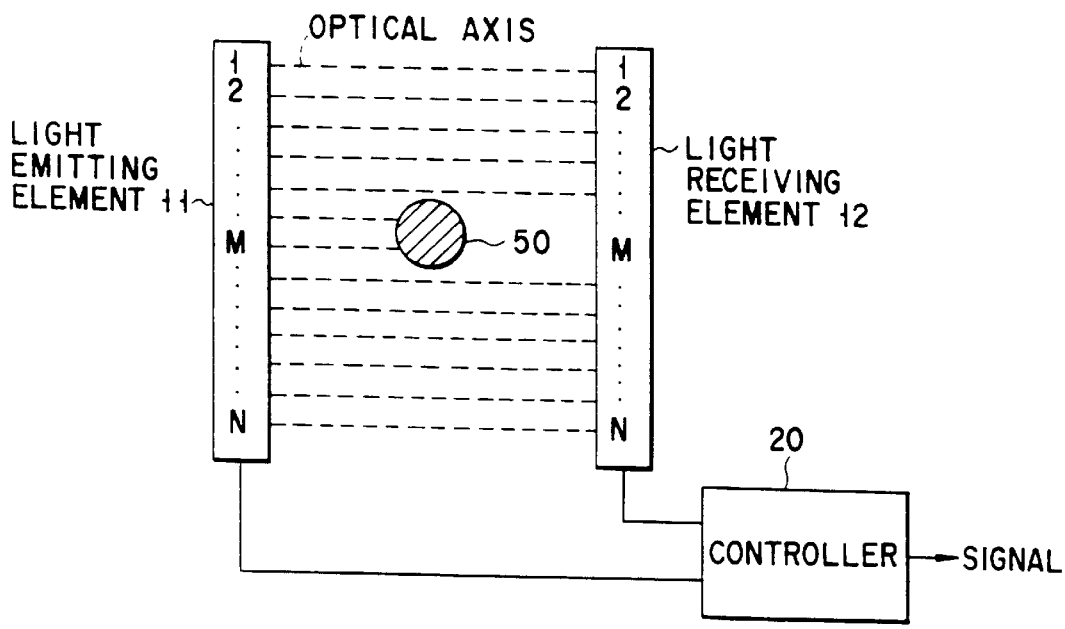
FIG. 2 is a schematic representation of a conventional senior.
Figure 3A:
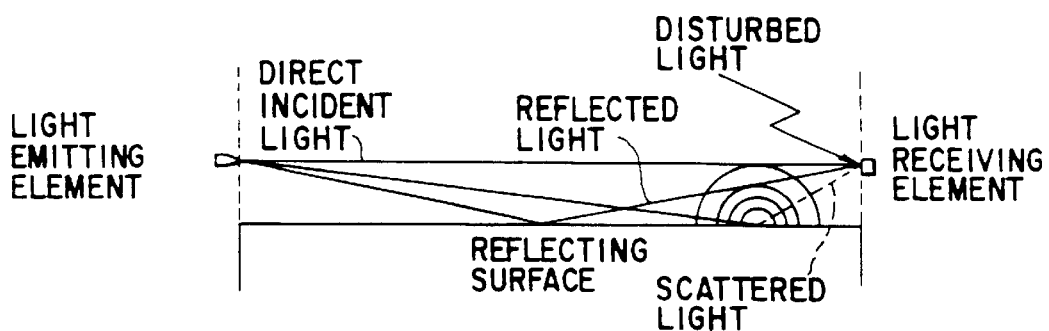
FIGS. 3A and 3B are diagrams for explaining the disadvantages of the conventional sensor.
Figure 3B:
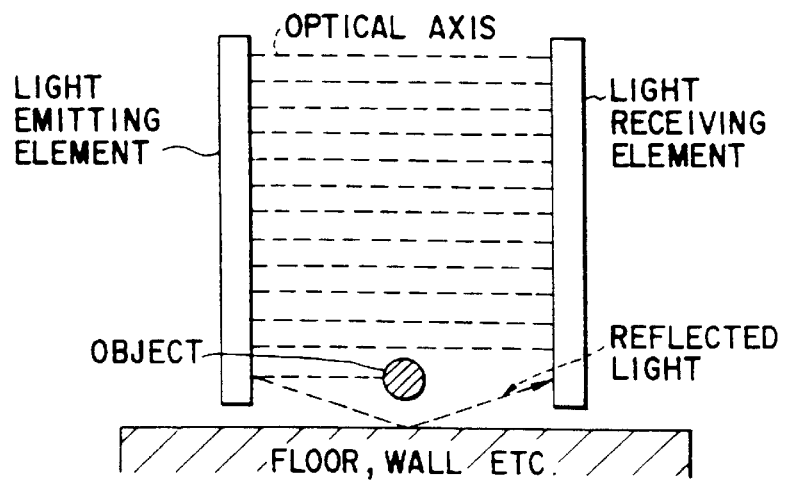

Embodiments of the present invention will be described, with reference to the accompanying drawings. In describing each embodiment, the components identical to those of any other embodiment will be designated at the identical reference numerals and will not be repeatedly described in detail.

Figure 4:
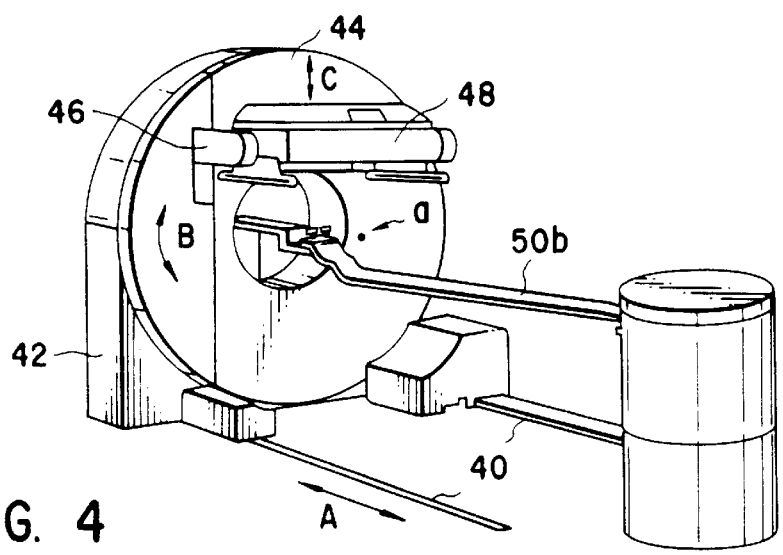
FIG. 4 is a perspective view showing a scintillation camera according to an embodiment of the present invention.

FIG. 4 shows a scintillation camera which is an embodiment of the present invention. More precisely, the figure shows the major components of the camera, such as a detector and a mechanism supporting the detector.

As shown in FIG. 4, two parallel stand rails 40 are laid on the floor. A stand 42 is mounted on the rails 40 and can move back and forth in the directions specified by A. A subject (not shown) lying on the bed 50b remains positioned with his or her body axis parallel to the directions A, while data is acquired from the subject. On one side of the stand 42, a rotating plate 44 is mounted, which can rotate in the directions specified by B. An arm 46 is secured at one end to the peripheral edge portion of the rotating plate 44. A detector 48 is attached to the other end of the arm 46. The detector 48 can rotate around the isocenter a, as the plate 44 rotates. The arm 46 include a mechanism (not shown) for moving the detector 48 toward and away from the subject in the directions indicated by C.

Sensors are attached to the detector 48, for detecting whether or not the detection surface (γ-ray incidence surface) of the detector 48 has approached the subject, at the body surface of the subject. The sensors may be of one of the various types which will be described below.

Figure 5A:
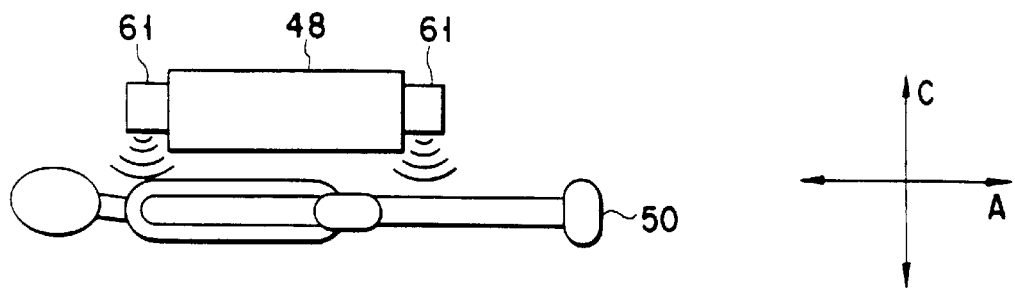
FIGS. 5A and 5B are diagrams showing the detector used in the camera of FIG. 4 and the ultrasonic sensors attached to the detector.
Figure 5B:
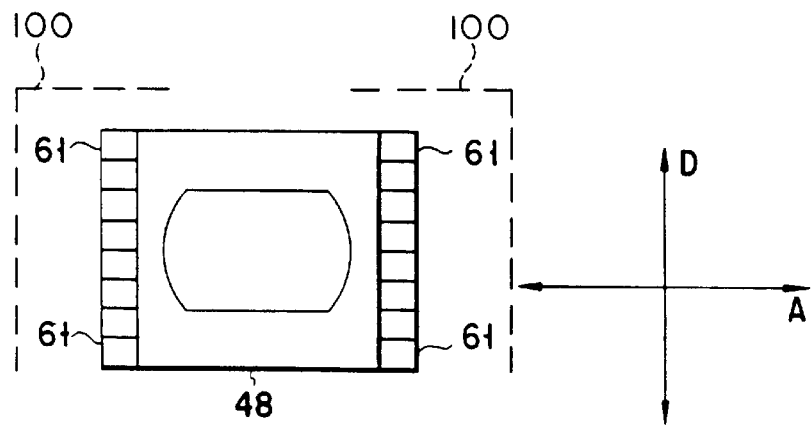

FIGS. 5A and 5B are diagrams showing the detector 48 and the ultrasonic sensors attached to the detector 48. More specifically, FIG. 5A is a side view showing the detector 48 and the ultrasonic sensor attached to the detector 48, and FIG. 5B is a bottom view showing the detector 48 and the ultrasonic sensor.

As shown in FIGS. 5A and 5B, two arrays of ultrasonic sensors 61 are attached to the front and rear of the detector 48, respectively. The arrays of sensors 61 extend parallel to each other, in the widthwise direction D (hereinafter referred to as "direction D") of a subject 50. Each ultrasonic sensor 61 emits ultrasonic waves to the body surface of the subject 50 and receives the waves reflected therefrom, measures the distance between it and the body surface from the time lapsing from the emission of waves to the receipt thereof, and produces a signal when the distance thus measured changes to a predetermined value.

The output signal of each ultrasonic sensor 61 is in an ON state when the detecting surface of the detector 48 approaches the subject 50, at a predetermined distance from the body surface of the subject 50, and is in an OFF state when the detecting surface of the detector 48 is located at a distance longer than the predetermined distance from the body surface of the subject 50. This definition of the ON state and OFF state of the output signal of each ultrasonic sensor 61 will be applied, unless otherwise specified, to all types of sensors used in the invention and which will be described later. A housing 100 is provided for housing the sensors 61 when not in use.

Figure 6:
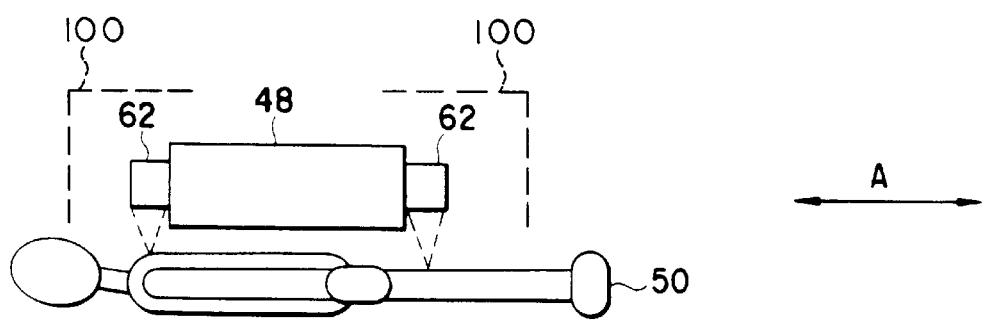
FIG. 6 is a side view showing the detector and the reflection type optical sensors attached to the detector.

FIG. 6 is a side view showing the detector 48 and the reflection-type optical sensors attached to the detector 48. As shown in FIG. 6, two arrays of reflection-type optical sensors 62 are attached to the front and rear of the detector 48, respectively, and extend parallel to each other, in the direction D, in the same way as the arrays of ultrasonic sensors 61 shown in FIGS. 5A and 5B. Each optical sensor 62 emits a light beam to the body surface of the subject 50 and receives the beam reflected therefrom, measures the distance between it and the body surface from the time lapsing from the emission of the light beam to the receipt thereof, and generates a signal when the distance thus measured changes to a predetermined value. A housing 100 is provided for housing the sensors 62 when not in use.

Figure 7:
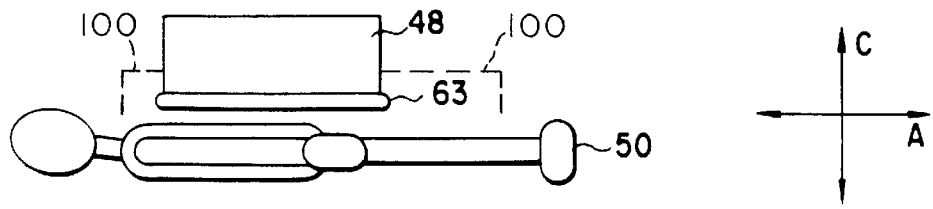
FIG. 7 is a side view showing the detector and the air-mat sensor attached to the detector.

FIG. 7 is a side view showing the detector 48 and an air-mat sensor. The air-mat sensor comprises an air mat 63 and an air-pressure sensor (not shown) contained in the air mat 63. The air mat 63 is attached to the detection surface of the detector 48, covering the entire detection surface and filled with air at a predetermined pressure. The air mat 63 has a uniform thickness, which is equal to the distance by which each of the ultrasonic sensors 61 (FIGS. 5A and 5B) or each of the optical sensors 62 (FIG. 6) is spaced apart from the body surface of the subject 50 when the sensor 61 or 62 produces a signal. When the air mat 63 contacts the subject 50, the air pressure in the mat 63 changes. The air-pressure sensor, contained in the air mat 63, detects this change in the air pressure and produces a detection signal. A housing 100 is provided for housing the sensor 63 when not in use.

Figure 8A:
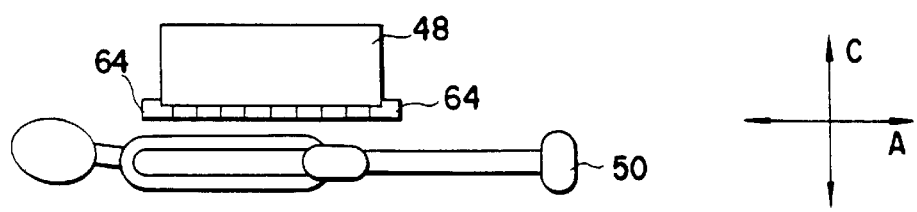
FIGS. 8A, 8B, and 8C ate diagrams showing the detector and the tension sensors connected to the detector.
Figure 8B:
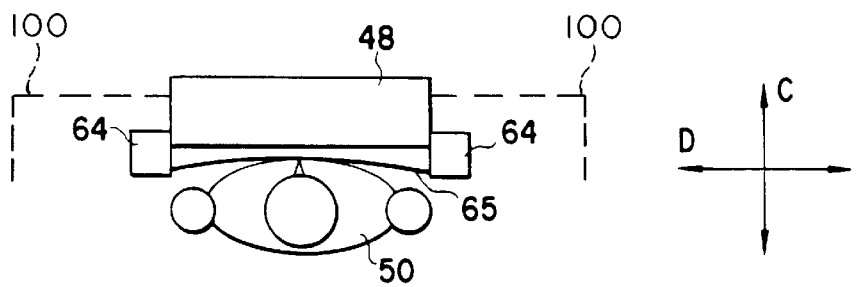
Figure 8C:
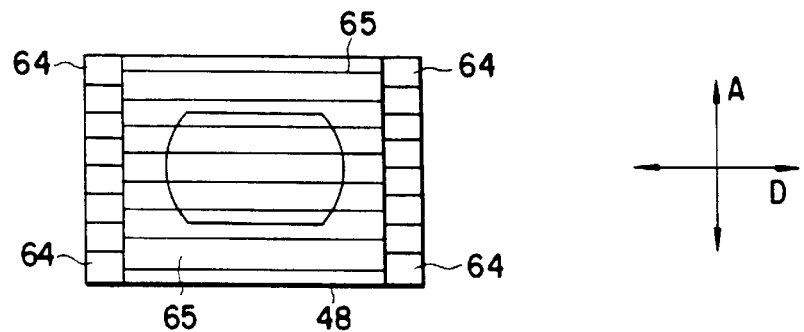

FIGS. 8A, 8B, and 8C are diagrams showing the detector 48 and the tension sensors 64 connected to the detector 48. More specifically, FIG. 8A is a side view showing the detector 48 and the tension sensors 64, FIG. 8B is a front view as seen from the head of a subject 50, and FIG. 8C is a bottom view of the detector 48. A housing 100 is provided for housing the sensors 64 when not in use.

A plurality of strings 56 are stretched beneath the detection surface of the detector 48, extending parallel to one another as shown in FIG. 8C. They are spaced away from the detection surface of the detector 48 by a predetermined distance. This distance is equal to the distance by which each of the ultrasonic sensors 61 (FIGS. 5A and 5B) or each of the optical sensors 62 (FIG. 6) is spaced apart from the body surface of the subject 50 when the sensor 61 or 62 produces a signal. Two tension sensors 64 are connected to the ends of one string 65. When the string 65 contacts a subject 50, its tension changes. The tension sensors 64 detects the change in tension and generate a detection signal. The strings 65 may be replaced by a strip of cloth.

Figure 9A:
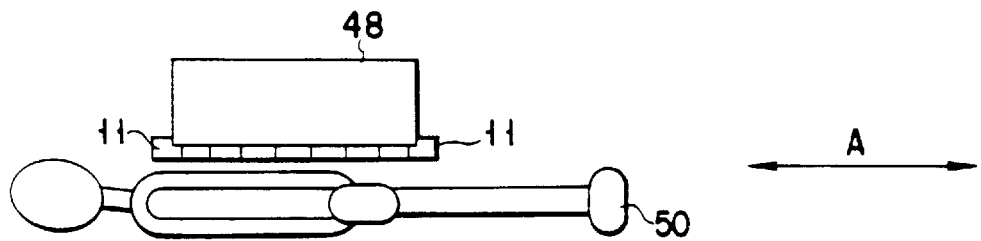
FIGS. 9A, 9B, and 9C are diagrams showing the detector and the counter-type/optical sensors connected to the detector.
Figure 9B:
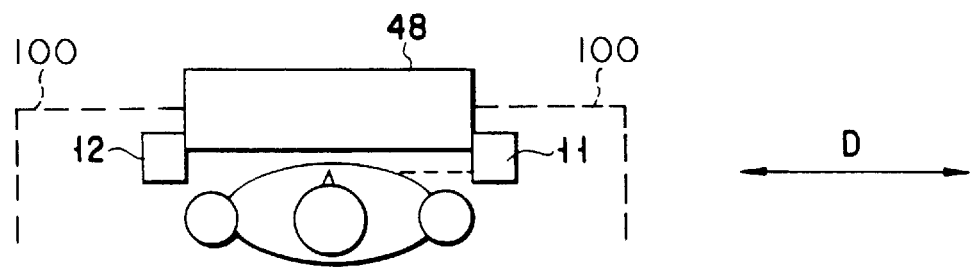
Figure 9C:
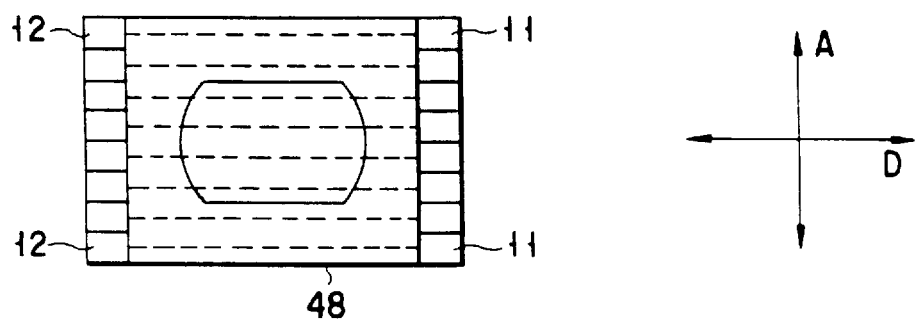

FIGS. 9A, 9B, and 9C are diagrams showing the detector 48 and the counter-type optical sensors connected to the detector 48. More specifically, FIG. 9A is a side view showing the detector 48 and the counter-type optical sensors, FIG. 9B is a front view as seen from the head of a subject 50, and FIG. 9C is a bottom view of the detector 48.

As shown in FIGS. 9A and 9B, an array of light-emitting elements 11 is connected to one side of the detector 48, and an array of light-receiving elements 12 to the other side of the detector 48. Both arrays extend in the direction indicated by A. Each of the counter-type optical sensors comprises a light-emitting element 11 and a light-receiving element 12. As shown in FIG. 9C, the optical axis of each counter-type optical sensor extends in the direction D and parallel to the optical axis of any other counter-type optical sensor. As can be seen from FIG. 9B, the optical axes of the counter-type optical sensors are spaced away from the detection surface of the detector 48 by a predetermined distance. This distance is equal to the distance by which each of the ultrasonic sensors 61 (FIGS. 5A and 5B) or each of the optical sensors 62 (FIG. 6) is spaced apart from the body surface of the subject 50 when the sensor 61 or 62 generates a signal. The output signal of each counter-type optical sensor is in an ON state when an object interrupts the light beam traveling from the light-emitting element 11 toward the light-receiving element 12, and is in an OFF state when no object interrupts the light beam. A housing 100 is provided for housing the light-emitting elements 11 and the light-receiving elements 12 when not in use.

Figure 10A:
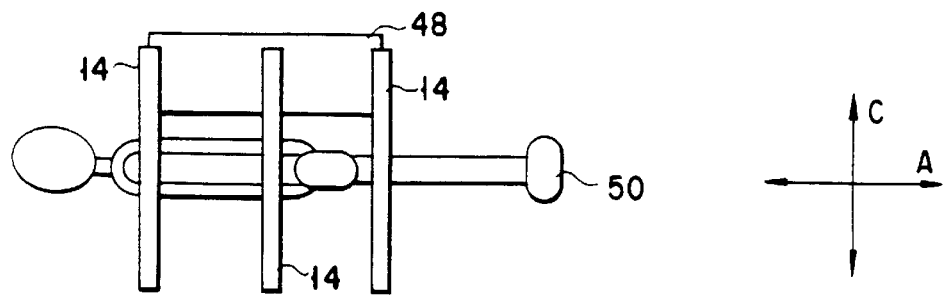
FIGS. 10A and 10B are diagrams showing the detector and the counter-type optical sensors attached to the detector.
Figure 10B:
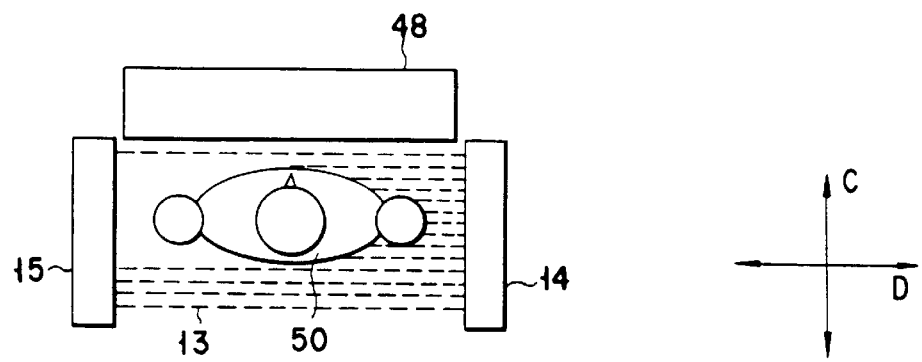

FIGS. 10A and 10B are diagrams showing the detector 48 and the counter-type optical sensors attached to the detector 48. More specifically, FIG. 10A is a side view showing the detector 48 and the counter-type optical sensors, and FIG. 10B is a front view as seen from the head of a subject 50.

As shown in FIG. 10A, three arrays 14 of light-emitting elements 11 stand on the floor, extending vertically and equidistantly spaced apart in the direction specified by A. Similarly, three arrays 15 of light-emitting elements 12 stand on the floor, extending vertically and equidistantly spaced apart in the direction indicated by A. As shown in FIG. 10B, the arrays 14 are spaced from the arrays 15 respectively, in the direction specified by D, by a distance longer than the width of the detector 48 and the body width of a subject 50.

Each of the counter-type optical sensors comprises a light-emitting element 11 of one array 14 and the associated light-receiving element 12 of the array 15 opposing the array 14. As shown in FIG. 10B, the optical axes 13 of the counter-type optical sensors extend in the direction D and parallel to one another, and are spaced apart, from one another, equidistantly. The out-put signal of each light-receiving element 12 decreases in magnitude when an object interrupts the light beam traveling from the associated light-emitting element 11 toward the light-receiving element 12. Hence, the number of the light-receiving elements 12, whose out-put signals have yet to decrease in magnitude, indicates the distance between the detection surface of the detector 48 and the body surface of the subject 50, since the optical axes 13 of the counter-type optical sensors are spaced apart from one another equidistantly.

The sensor system shown in FIGS. 10A and 10B is in an ON state when the detection surface of the detector 48 is spaced apart from the body surface of the subject 50 by a predetermined distance, and is in an OFF state when the detection surface of the detector 48 is spaced apart from the body surface of the subject 50 by a distance longer than the predetermined one. The predetermined distance is equal to the distance by which each of the ultrasonic sensors 61 (FIGS. 5A and 5B) or each of the optical sensors 62 (FIG. 6) is spaced apart from the body surface of the subject 50, when the sensor 61 or 62 produces a signal. Neither the arrays 14 of light-emitting elements nor the arrays 15 of light-receiving elements need to stand on the floor. Instead, they may be secured to the sides of the detector 48 so as to move as the detector 48 is moved in the directions specified by A. Furthermore, the three arrays 14 may be replaced by three light-emitting elements 11, and the three arrays 15 by three light-receiving elements 12 opposing the three light-emitting elements 11, respectively, provided that each pair of the associated elements 11 and 12 move in the directions indicated by C to scan the subject 50, along his or her side.

In the present embodiment, sensors of any one of the types described above with reference to FIGS. 5A to 10B can be employed. Sensors of any type described above can also be used in other embodiments of the invention, which will be described below.

Figure 11:
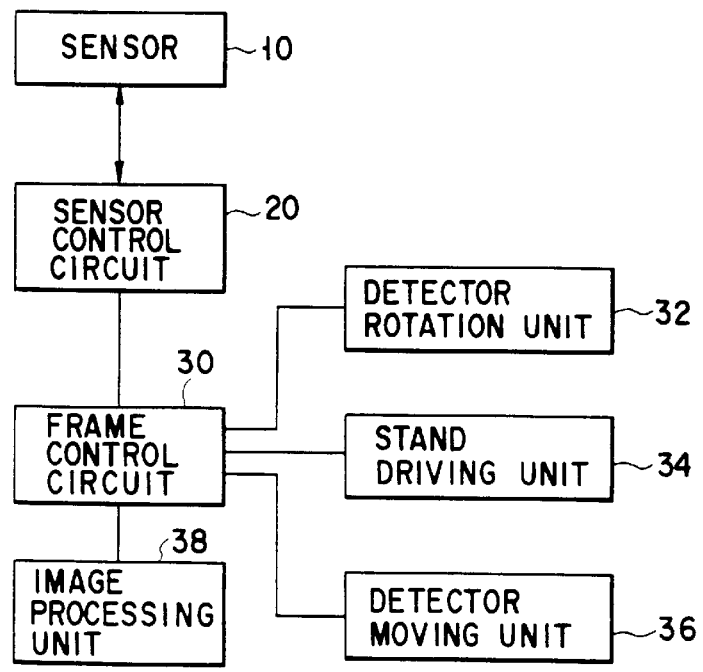
FIG. 11 is a block diagram showing a scintillation camera according to a first embodiment of the present invention.
Figure 12:
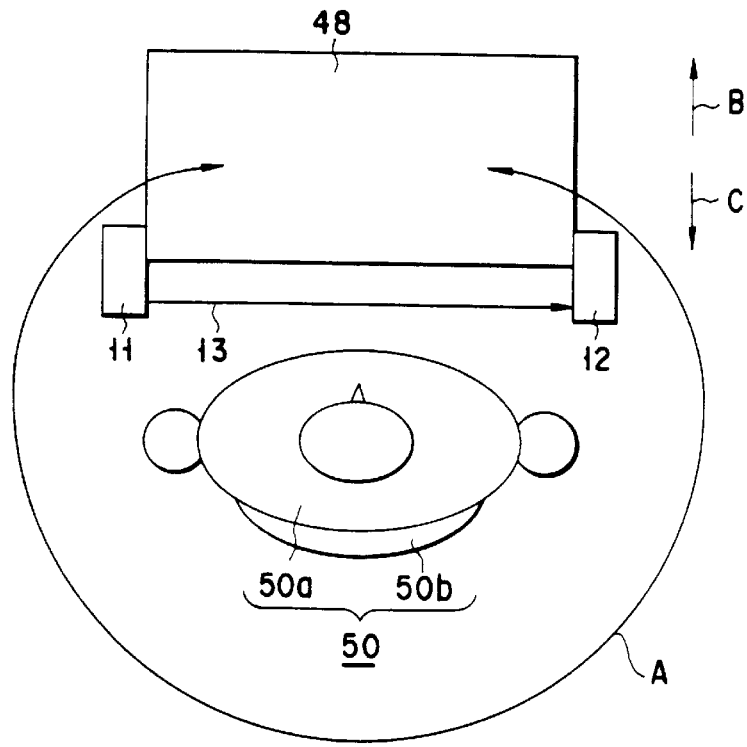
FIG. 12 is a diagram illustrating the positional relationship between a subject and the detector incorporated in the scintillation camera.

FIG. 11 is a block diagram illustrating a scintillation camera according to a first embodiment of the present invention. FIG. 12 shows the positional relationship between a subject 50 and the detector 48 incorporated in the scintillation camera.

As shown in FIG. 11, the scintillation camera comprises a sensor 10, a sensor control circuit 20, a frame control circuit 30, a detector rotating unit 32, a stand driving unit 34, a detector moving unit 36 and an image processing unit 38. The sensor 10 is of any one of the types described above. The sensor control circuit 20 is designed to detect whether the sensor 10 is in an ON state or an OFF and to turn on and off each of the light-emitting elements and each of the light-receiving elements, all incorporated in the sensor 10. The frame control circuit 30 is used to control the motion of the frame (not shown) of the scintillation camera. The detector rotating unit 32 is provided for rotating the detector 48 mounted on the frame. The stand driving unit 34 is designed to move the stand of the scintillation camera horizontally. The detector moving unit 36 is provided for moving the detector 48 toward and away from a subject 50a (FIG. 12) or a bed 50b (FIG. 12) on which the subject 50a is lying, so that the detector 48 may remain at a predetermined distance from the subject 50a or from the bed 50b. The image processing unit 38 is designed to process the image data acquired by the detector 48.

The operation of the scintillation camera shown in FIG. 11 will be described, based on the assumption that the sensor 10 is a counter-type optical sensor of the type shown in FIGS. 9A to 9C though it may be of any other type described above.

The sensor control circuit 20 drives the first to Nth sensor units of the sensor 10, each consisting of a light-emitting element and a light-receiving element—at high speed one after another. The circuit 20 detects whether each sensor unit is on or off, and supplies the frame control circuit 30 with data which represents that each sensor unit is in an ON state or an OFF state. Since their ON/OFF states are detected at high speed, the first to Nth sensor units jointly operate as if they were a single sensor, which is the sensor 10.

The frame control circuit 30 controls the detector rotating unit 32, the stand driving unit 34 and the detector moving unit 36 in accordance with the data supplied from the sensor control circuit 20 and predetermined data-acquisition conditions, to thereby move the detector 48 in a desired manner with respect to the subject 50a and the bed 50b. Under the control of the circuit 30, the detector rotating unit 32 rotates the detector 48 around the subject 50a and the bed 50b in the directions specified by A, the stand driving unit 34 moves the stand 42 (FIG. 4), thereby moving the detector 48 in the direction D, and the detector moving unit 36 moves the detector 48 away from the subject 50a and the bed 50b in the direction of arrow B or toward the subject 50a and the bed 50b in the direction of arrow C. Thus rotated and linearly driven, the detector 48 moves around the subject 50a and 50b in a desired orbit. In the description that follows, the motion of the detector 48 in the directions indicated by A will be referred to as "rotation," that of the detector 48 in the direction of arrow B as "far," and that of the detector 48 in the direction of arrow C as "near."

In the scintillation camera, as already indicated, the frame control circuit 30 controls the detector moving unit 36 in accordance with the ON/OFF state of the sensor 10. Hence, the detector 48 make a far or a near motion thereby so as to be located at a predetermined distance away from the body surface of the subject 50a or from the bed 50b.

Every time the detector 48 is rotated at a predetermined angle, for example, 90°, it acquires the data representing the positions of the subject 50a and the bed 50b. The position data is supplied to the image processing unit 38. The unit 38 extracts data, representing the ridge line of the subject 50a, from the position data which the detector 48 acquires as it rotates once around the subject 50a and the bed 50b. The ridge-line data, which shows the ridge line with precision, can be used as absorption-correcting data.

Figure 13A:
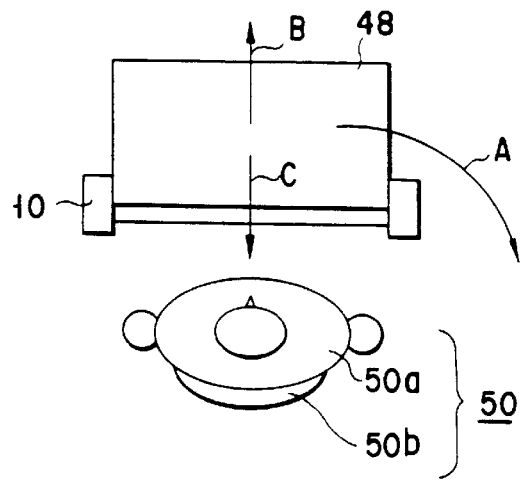
FIGS. 13A and 13B are diagrams schematically illustrating the detector section of the scintillation camera.
Figure 13B:
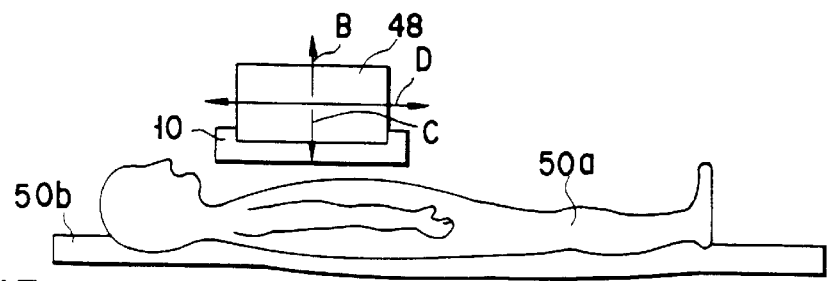

How the detector 48 is moved to a prescribed position to acquire data from the subject 50a will be described in detail, with reference to FIGS. 13A and 13B. The components identical to those shown in FIG. 12 are denoted by the same numerals in FIGS. 13A and 13B and will not be described in detail. Like FIG. 12, FIG. 13A is a front view as seen from the head of a subject 50a. FIG. 13B is a side view.

As the detector 48 is moved in the directions indicated by arrows A, B, C, and D shown in FIGS. 13A and 13B, the sensor control circuit 20 keeps monitoring the ON/OFF state of the sensor 10. The circuit 20 supplies the frame control circuit 30 with the data showing that the sensor 10 is in the ON state or the OFF state. The circuit 30 controls the detector moving unit 36 in accordance with the data so that the detector 48 may be located at a predetermined distance from the body surface of the subject 50a or from the bed 50b. Arrows D in FIG. 13B indicate the opposite directions in which the detector 48 is moved along the body axis of the subject 50a, from head to toe and other way around.

The detector 48 may contact the subject 50a or the bed 50b on the bed 50b while being rotated in either of the directions of arrow A, while being moved in either of the horizontal directions of arrow D, or while approaching the subject 50a in the direction of arrow C. Nonetheless, it is unnecessary for an operator of the scintillation camera to take pains to prevent the detector 48, from contacting the subject 50a or the bed 50b. This is because the sensor 10 attached to the detector 48 serves to locate, as described above, the detector 48 always at the predetermined distance from the body surface of the subject 50a or from the bed 50b.

More specifically, when the sensor 10 detects the subject 50a or the bed 50b while the detector 48 is being rotated in either direction of arrow A, the detector 48 automatically makes a far motion. When the sensor 10 detects the subject 50a or the bed 50b while the detector 48 is being moved parallel to the subject 50a or the bed 50b in either direction of arrow D, the detector 48 automatically makes a far motion. When the sensor 10 detects the subject 50a or the bed 50b while the detector 48 is approaching the subject 50a or the bed 50b in the direction of arrow C, the detector 48 is automatically stopped.

Since the detector 48 stops approaching the subject 50a or the bed 50b or retreats therefrom in accordance with the ON/OFF state of the sensor 10 which is detected while the detector 48 is rotating and horizontally moving, the operator can move the detector 48 to a desired position within a short time, without taking pains not to let the detector 48 contact the subject 50a or the bed 50b.

Figure 14:
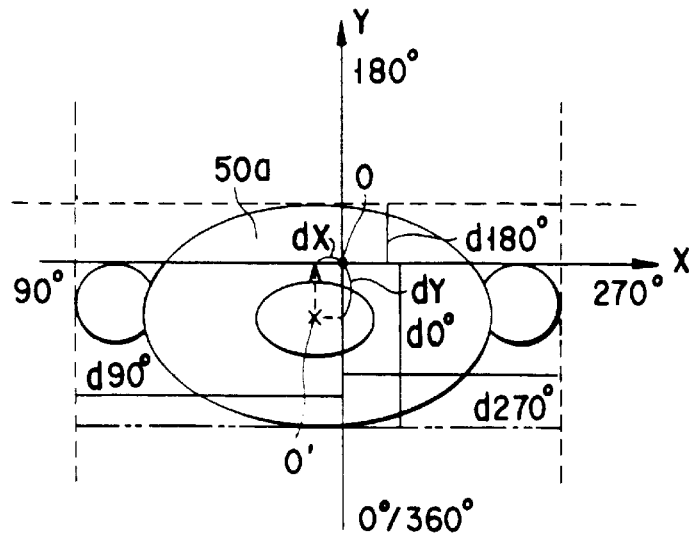
FIG. 14 a schematic representation of a subject, for explaining how to locate the body axis of the subject.

It will now be explained how to locate the body axis of the subject 50a with the scintillation camera, with reference to FIGS. 14 and 15. FIG. 14 is a schematic representation of the subject 50a, as viewed from the head. FIG. 15 is a flow chart for explaining the method of locating the body axis. In FIG. 14, the center of rotation of the detector 48 is designated as point O, and the body axis located by computation is denoted as point O'.

As the detector 48 rotates around the subject 50a, clockwise in FIG. 14, it assumes a 0°-position at the back of the subject, a 90°-position on the left side of the subject, a 180°-position in front of the subject, a 270°-position on the right side of the subject, a 360°-position (identical to the 0°-position) at the back of the subject.

Referring to FIG. 15, the detector 48 is rotated to the 0°-position in Step A1. Next, in Step A2, the detector 48 is made to approach the bed 50b until the sensor 10 detects the ON state. In Step A3, the detector 48 is stopped when the sensor 10 detects the ON state, and the data representing the position of the detector 48, i.e., x-axis coordinate value and y-axis coordinate value, is stored into a memory. Then, in Step A4, the detector 48 is rotated clockwise through 90°. In Step A5, it is determined whether or not the detector 47 has been rotated through 360° around the subject 50a, and back to the 0°-position. If Not in step A5, the flow returns to Step A2. If it has, the flow goes to Step A6, in which the following values dx and dy are calculated:

$$dx = (d270° - d90°)/2$$

$$dy = (d180° - d0°)/2$$

where d0°, d90°, d180° and d270° are the XY-coordinate positions the center of the detector 48 takes, as the detector 48 move to the 0°-position, the 90°-position, the 180°-position and the 270°-position, respectively.

Thanks to the use of the sensor control circuit 20 and the like, which serve to keep the detector 48 spaced apart from the subject 50a, it is possible to automatically acquire data items dx and dy, which correctly define the position of the body axis O' of the subject 50a.

A device (not shown) designed to adjust the position of the subject 50a is operated until the distance between the center O of rotation of the detector 48 and the body axis O' thus located is reduced to nil. As a result of this, the subject 50a is automatically placed in a desirable position with respect to the detector 48 —that is, he or she is positioned with the body axis passing through the center O of rotation of the detector 48. Since the subject 50a has been detected the desirable position, the detector 48 can then proceed to acquire accurate data from the subject 50a. The data are so accurate that a tomographic image of the subject, reconstructed from the data, will have high quality. Furthermore, once the subject 50a has been placed at the desirable position, it is no longer necessary for the operator to make far or near motion of the detector 48 to the subject 50a. Thus, the scintillation camera can acquire data from the subject 50a with high efficiency.

A scintillation camera according to a second embodiment, which is designed for use in a single photon emission computed tomography apparatus (hereinafter referred to as "SPECT apparatus"), will be described in the following.

This scintillation camera is similar in structure to the scintillation camera shown in FIG. 11, and its structure, therefore, will not be described in detail. The camera can acquire SPECT data from a subject in two modes, i.e., stepwise data-acquisition mode and continuous data-acquisition mode. In the stepwise data-acquisition mode, the detector acquires SPECT data every time it is stopped after it has been rotated through a prescribed angle of, for example, 60°. In the continuous data-acquisition mode, the detector continuously acquires data while rotating around the subject without pause.

The stepwise acquisition of SPECT data will be described in greater detail, with reference to FIGS. 16 to 20.

Figure 16:
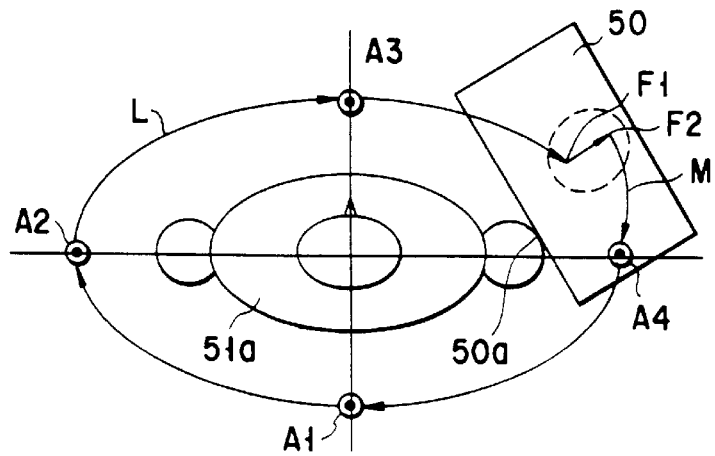
FIG. 16 is a diagram schematically showing a subject, for explaining how SPECT data is acquired from the subject in stepwise mode by a conventional scintillation camera.
Figure 17:
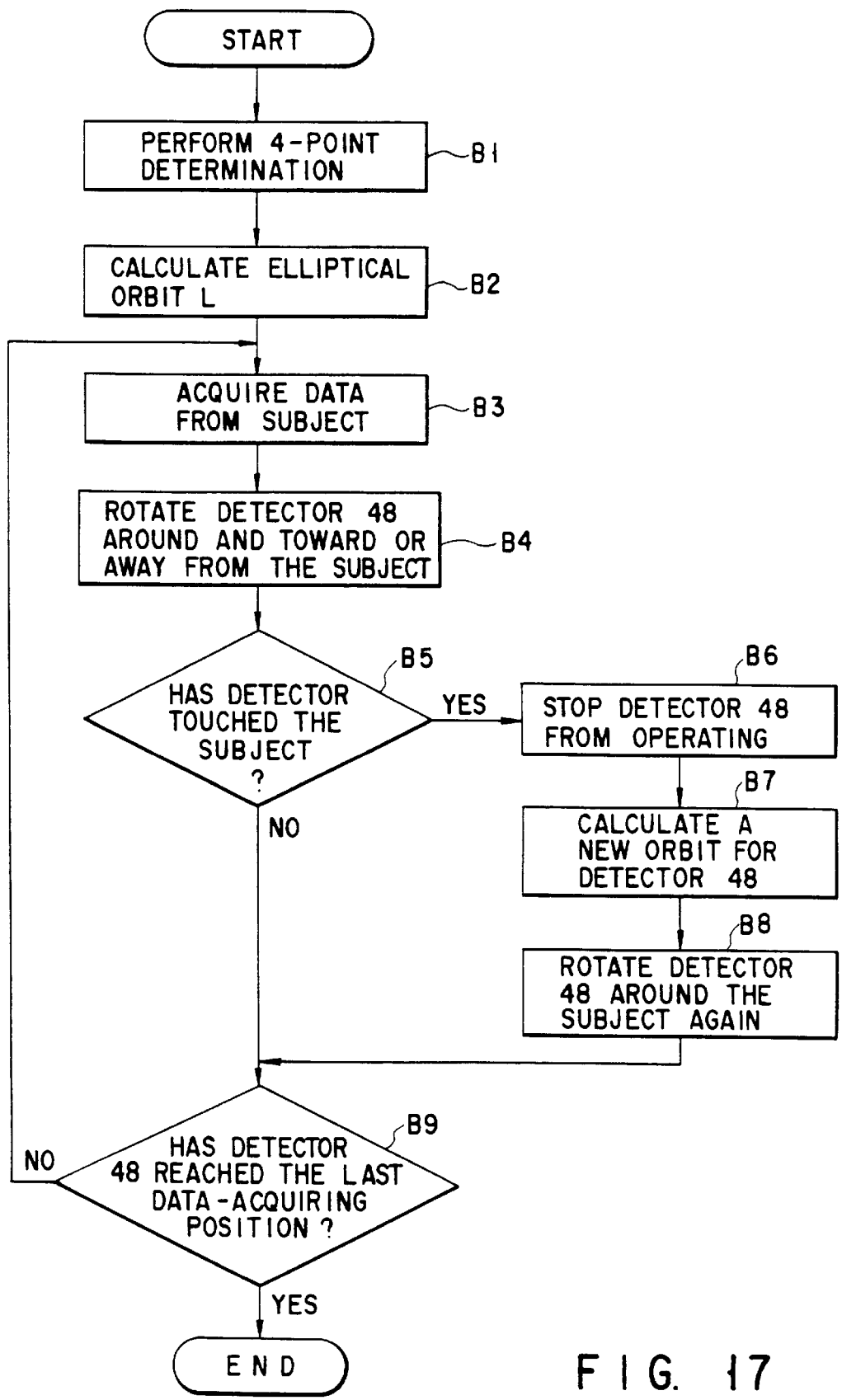
FIG. 17 is a flow chart for explaining how the conventional scintillation camera is operated to acquire SPECT data from ye subject in the stepwise mode.

How the conventional scintillation camera acquires SPECT data in the stepwise mode will be first described, with reference to FIGS. 16 and 17. FIG. 16 is a diagram schematically showing a subject, for explaining how SPECT data is acquired from the subject in stepwise mode by a conventional scintillation camera. FIG. 17 is a flow chart for explaining how the conventional scintillation camera is operated to acquire SPECT data from the subject in the stepwise mode.

Referring to the flow chart of FIG. 17, the aforementioned 4-point determination method is performed in Step B1 in preparation for the acquisition of SPECT data. That is, as is shown in FIG. 16, the data items representative of four data-acquisition positions Al to A4, angularly spaced apart by 90°, are input before the detector of the camera is moved around a subject 50a to scan the subject. Next, in Step B2, an elliptical orbit L, in which the detector 48 is to move stepwise, to acquire SPECT data from the subject 50a, is calculated. Then, in Step B3, the detector 48 staying at the data-acquisition position A3, for example, starts acquiring SPECT data from the subject 50a. In Step B4, the detector 48 is rotated toward the next data-acquisition position A4 in the orbit L, and is simultaneously moved toward or away from the subject 50a. In Step B5, the contact sensor secured to the detector 48 determines whether or not the detection surface 48a of the detector has touched the body surface of the subject 50a or the bed 50b during the transit from the position A3 to the position A4. If Yes, the flow goes to Step B6, in which the detector 48 is moved away from the subject 50a. More precisely, as shown in FIG. 16, the detector 48 is stopped from rotating around the subject 50a at point F1 lying on the orbit L and located between the positions A3 and A4. Then, it makes a far motion to point F2. Next, in Step B7, a new elliptical orbit M is calculated, which passes both points F2 and A4. In Step B8, the detector 48 is rotated around the subject 50a from point F2 to the position A4 along the new elliptical orbit M.

If No in Step B5, that is, if the detector 48 has not touched the body surface of the subject 50a or the bed 50bduring the transit from the data-acquisition position A3 to position A4, then the flow jumps to Step B9. In Step B9, it is determined whether or not the detector 48 has reached the last data-acquisition position. If No, the flow returns to Step B3. If Yes, the acquisition of the SPECT data is terminated.

Figure 18:
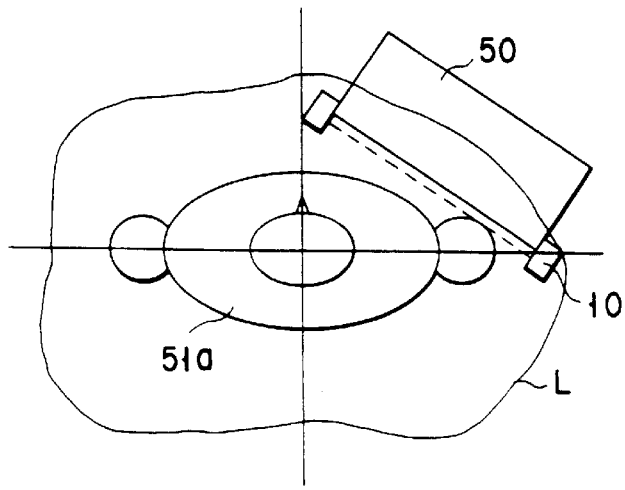
FIG. 18 is a diagram schematically showing a subject, for explaining how SPECT data is acquired from the subject in the stepwise mode by the scintillation camera according to a second embodiment of the invention.

With the scintillation camera according to the second embodiment of this invention, no steps whatsoever, equivalent to Steps B1 and B2, need be performed as will be explained in the following, with reference to FIGS. 18, 19 and 20. FIG. 18 is a diagram schematically showing a subject, for explaining how SPECT data is acquired from the subject in the stepwise mode by the scintillation camera. FIG. 19 is a flow chart for explaining how the camera is operated to acquire SPECT data from the subject in the stepwise mode. FIG. 20 is a flow chart explaining, in detail, Step C7 which is one of the steps for operating the camera.

With reference to FIGS. 18 and 19 it will be explained how the scintillation camera acquires SPECT data from the subject in the stepwise mode.

As has been indicated, the data acquisition is started without performing the 4-point determination method. First, in Step C1, the sensor control circuit 20 determines whether the sensor 10 detects an ON state or an OFF state, as illustrated in FIG. 18. If the sensor 10 is in the OFF state, the flow goes to Step C2, in which the detector 48 makes near motion to the subject 50a. In Step C3, it is determined whether the sensor 10 has detected the ON state or the OFF state. If the sensor 10 is in the OFF state, the flow returns to Step C3. If the sensor 10 is in the ON state, the flow goes to Step C4, in which the detector 48 is stopped from rotating around the subject 50a. Then, the flow goes to Step C5.

In Step C5, the data representing the position at which the detector 48 is stopped is stored into a storage device (not shown). Not only the data, but also any other data showing the position the detector 48 will detect every time it is rotated around the subject 39a through a predetermined angle is stored into the storage device. These data items define the ridge line of the subject and can be used as absorption-correcting data. Hence, the ridge line of the subject is automatically obtained.

Then, in Step C6, the detector acquires SPECT data from the subject for a predetermined period of time. In Step C7, the detector 48 is automatically rotated around the subject and moved with respect thereto in accordance with the ON/OFF state of the sensor 10, as will be described later in detail. In Step C8, it is determined whether or not the detector 48 has reached the position where it should stop acquiring SPECT data. If Yes, the detector 48 stops acquiring the SPECT data. If No, the flow returns to step C5.

With reference to FIG. 20, Step C7 will be explained in more detail, in which the detector is automatically rotated around the subject and moved with respect thereto, in accordance with the ON/OFF state of the sensor 10.

First, in Step D1 the detector 48 is rotated around the subject toward the next data-acquisition position. In Step D2, it is determined whether the sensor 10 is in the ON state or the OFF state while the detector 48 is being rotated. If the sensor 10 is in the ON state, the flow goes to Step D6. If the sensor 10 is in the OFF state, the flow goes to Step D3. The detector 48 keeps rotating, unlike the conventional scintillation camera.

If it is detected in Step D2 that the sensor 10 is in the OFF state, the sensor control circuit 20 detects that the detector is spaced away from the subject. Hence, Step D3 is performed, in which the detector 48 starts near motion to the subject. In Step D4, it is determined whether the sensor 10 has detected the ON state or the OFF state. If the sensor 10 is in the ON state, the flow goes to Step D5, in which the detector is made to stop near motion to the subject.

If it is detected in Step D2 that the sensor 10 is in the OFF state, indicating the possibility that the detector 48 may contact the subject 50a, the flow goes to Step D6. In Step D6, the detector 48 starts far motion from the subject 50a. In Step D7, it is determined whether the sensor 10 has detected the ON state or the OFF state. If the sensor 10 is in the ON state, the flow goes to Step D8, in which the detector is stopped from far motion from the subject. If the sensor 10 is in OFF state, the flow returns to Step D7. Thus, the detector makes far motion from the subject until it reaches a position at a predetermined distance from the subject.

Then, in Step D9, it is determined whether or not the detector 48 has reached the next data-acquisition position. If No, the flow returns to Step D2. If Yes, the detector 48 is stopped from rotating, and the flow goes to Step D10. In Step D10, it is determined whether the sensor 10 has detected the ON state or the OFF state. If the sensor 10 is in the ON state, that is, if the detector is located very close to the subject 50a or the bed 50b, Step C7 is terminated. If the sensor 10 is in the OFF state, that is, if the detector is at a long distance from the subject 50a or the bed 50b, the flow goes to Step D11, in which the detector 48 is made to near motion to the subject 50a or the bed 50b. In Step D12, it is determined whether the sensor 10 has detected the ON state or the OFF state. If the sensor 10 is in the OFF state, Step D12 is repeated until the sensor 10 detects the ON state. When the sensor 10 detects the ON state, the flow goes to Step D13, in which the detector 48 is stopped from near motion the subject 50a or the bed 50b.

Until the detector 48 reaches the last data-acquisition position, it is rotated around the subject 50a in the orbit L as illustrated in FIG. 18. When the detector 48 reaches the last data-acquisition position, the SPECT data of the subject 50a and the bed 50b and the ridge line data thereof have already been obtained.

After the near motion of the detector 48 to the subject 50a and the far motion thereof from the subject 50a (for example, after Step D5, Step D8 and Step D13), a delay may be provided so that the detector 48 need not make any unnecessary minute motion, such as inching motion. Moreover, the detector 48 can be rotated in an accurate orbit around the subject 50a, since it is automatically moved toward and away from the subject 50a at an appropriate speed. Thus, the detector is prevented from contacting the subject 50a or the bed 50b.

According to the present invention, the sensor 10 may obtain area data while the detector 48 is retreating from the subject 50a, and the area data may be stored into a memory (not shown). If the amount of area data increases, the speed at which the detector is retreating is increased, to thereby prevent the detector 48 from contacting the subject 50a or the bed 50b. In this case, the detector can be continuously moved even if the subject moves, to an optimal position with respect to the subject who has just moved.

Figure 21:
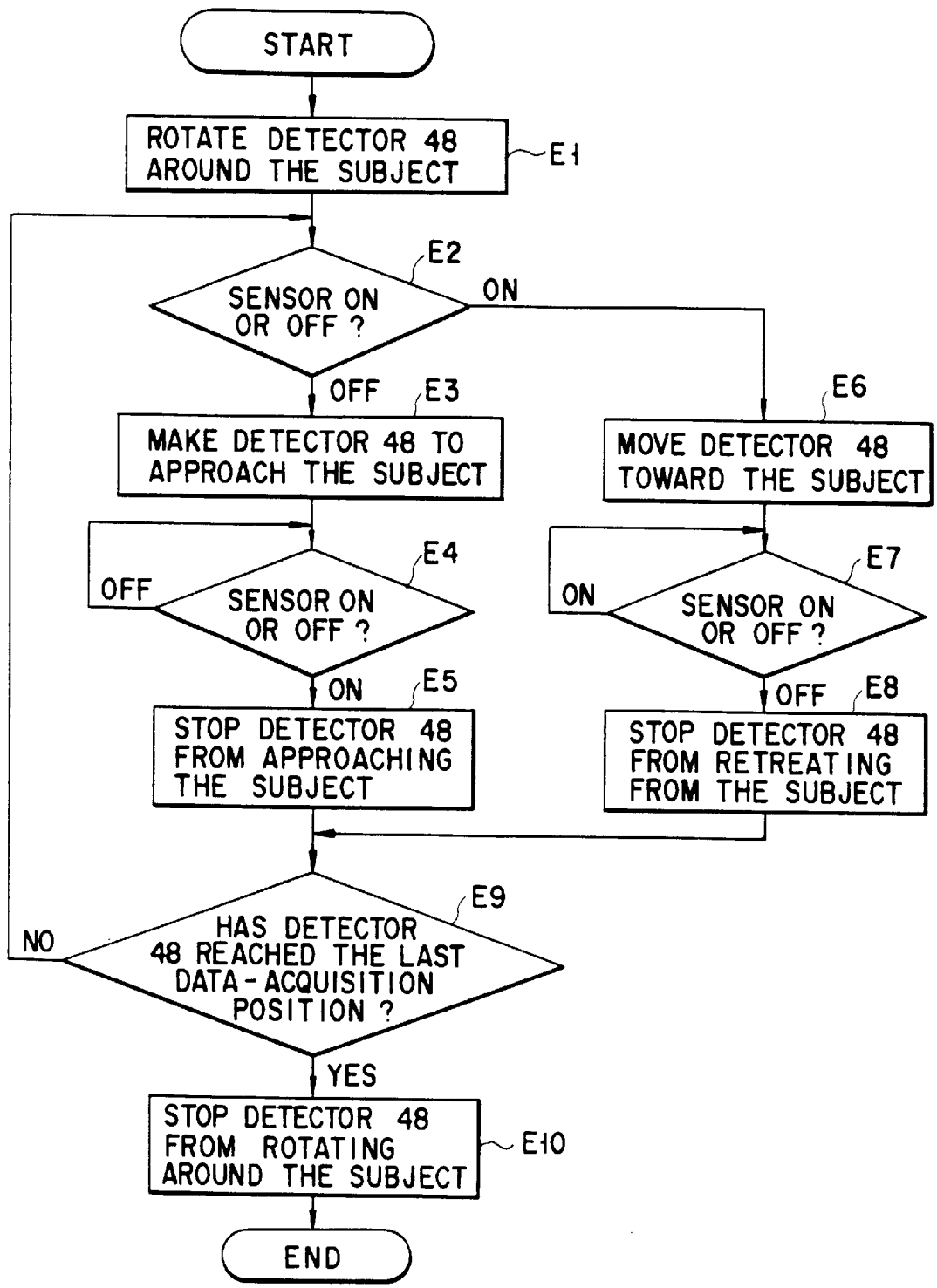
FIG. 21 is a flow chart for explaining how the scintillation camera, according to the second embodiment of the invention, is operated in order to acquire SPECT data from the subject in the continuous mode.

With reference to FIG. 21, it will be described how the scintillation camera of the invention acquires SPECT data from a subject in the continuous data-acquisition mode.

First, in Step E1 the detector 48 starts to rotate around the subject 50a and simultaneously begins acquiring SPECT data from the subject 50a. In Step E2, it is determined whether the sensor 10 has detected the ON state or the OFF state. If the sensor 10 is in the ON state, the flow goes to Step E6. If the sensor 10 is in the OFF state, the flow goes to Step E4. In Step E3 or Step E6, the detector 48 is not stopped from rotating, unlike the conventional data-acquisition method illustrated in FIG. 17.

If it is determined in Step E2 that the sensor 10 is in the OFF state, the sensor control circuit 20 detects that the detector 48 is spaced away from the subject. Hence, Step E3 is performed, in which the detector 48 is started on a near motion toward the subject. In Step E4, it is determined whether the sensor 10 has detected the ON state or the OFF state. If the sensor 10 is in the OFF state, Step E4 is repeated until the sensor 10 detects the ON state. When the sensor 10 detects the ON state, the flow goes to Step E5, in which the detector 48 is stopped from near motion to the subject 50a.

If it is determined in Step E2 that the sensor 10 is in the OFF state, there is the possibility that the detector could be about to contact the subject 50a or the bed 50b. Thus, in Step E6 the detector 48 is started on a far motion from the subject 50a. In Step E7 it is determined whether the detector 48 has detected the ON state or the OFF state. If the sensor 10 is in the ON state, Step E7 is repeated until the sensor 10 detects the OFF state. When the sensor 10 detects the OFF state, the flow goes to Step E8, in which the detector 48 is stopped from far motion from the subject 50a.

The flow goes from Step E5 or E6 to Step E9, in which it is determined whether or not the detector 48 has reached the last data-acquisition position. If No, the flow returns to Step E2. If Yes, the flow goes to Step E10, in which the detector 48 is stopped from rotating around the subject 50a.

During the continuous rotation of the detector 48, a data item representing the position of the detector 48 is obtained every time it is rotated around the subject 39a, through a prescribed angle. The data items thus obtained, while the detector 48 is rotating are stored into a storage device. These data items define the ridge line of the subject and can be used as absorption-correcting data. Hence, the ridge line of the subject is automatically obtained.

Also in the continuous data-acquisition mode, a delay may be provided after the near motion of the detector 48 to the subject 50a and the far motion thereof from the subject 50a (for example, after Step E5 and Step E8), so that the detector 48 need not make an unnecessary minute motion, such as inching motion. Moreover, the detector 48 can be rotated along an accurate orbit around the subject 50a since it is automatically moved toward and away from the subject 50a at an appropriate speed. Thus, the detector is prevented from contacting the subject 50a or the bed 50b.

In the continuous data-acquisition mode, as well, the sensor 10 may obtain area data while the detector 48 makes far motion from the subject 50a, and the area data may be stored into a memory (not shown). If the area data increases in amount, the speed at which the detector is retreating is increased, to thereby prevent the detector 48 from contacting the subject 50a or the bed 50b. In this case, the detector can be continuously moved even if the subject moves, to an optimal position with respect to the subject who has just moved.

In the embodiments described above, the detector 48 acquires SPECT data from the subject 50a while it is being rotated around the subject 50a, either intermittently or continuously. According to the present invention, a detector may be moved horizontally along the body axis of a subject, as will be described with reference to the flow chart of FIG. 22.

First, the data showing a scanning termination position is input by operating a console (not shown). In Step F1, the stand driving unit 34 starts moving the stand 42 in a horizontal direction, thereby moving the detector 48 in the same direction. While being so moved, the detector 48 keeps scanning a subject 50a and detecting the gamma-rays emitted from the radioisotope administered to the subject 50a.

In Step F2, the sensor control circuit 20 determines whether the sensor 10 has detected an ON state or an OFF state while the detector 48 is being moved horizontally. If the sensor 10 is in the OFF state, that is, if the detector 48 is at a predetermined distance from the subject 50a, the flow goes to Step F3, in which the detector moving unit 36 (FIG. 11) moves the detector 48 toward the subject 50a. In Step F4, it is determined whether the sensor 10 has detected the ON state or the OFF state. If the sensor 10 is in the OFF state, Steps F3 and F4 are repeated until the sensor 10 detects the ON state. When the detector 48 is moved to a predetermined distance from the subject 50a, the sensor 10 detects the ON state. Then, the flow goes to Step F5, in which the detector 48 is stopped from near motion to the subject 50a.

Next, in Step F6 the detector moving unit 36 starts moving the detector 48 away from the subject 50a. In Step F7, it is determined whether the sensor 10 has detected the ON state or the OFF state. If the sensor 10 is in the ON state, Step F6 and F7 are repeated until the sensor 10 detects the OFF state. In Step F8, the detector 48 is moved further away from the subject 50a for a predetermined time after the sensor 10 has detected the OFF state. In Step F9, upon elapse of the predetermined time, the detector 48 is stopped from far motion from the subject 50a. Then, the flow returns to Step F3, in which the detector 48 is started on a near motion to the subject 50a.

Steps F6 to F9 will be explained in greater detail, with reference to the flow chart of FIG. 23.

Figure 23:
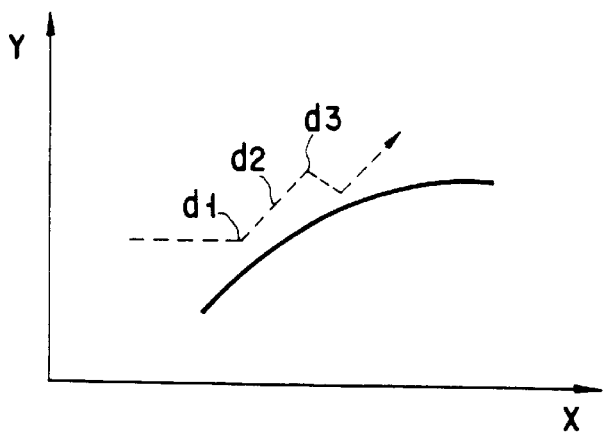
FIG. 23 is a diagram for explaining a method of preventing an inching motion during the scanning operation.

In FIG. 23, the solid line indicates a part of the ridge line of the subject 50a, and the broken line represents the path along which the detector 48 is moved. Further, in FIG. 23, point d1 indicates the position the detector 48 takes as it starts faring in Step F6, point d2 the position the detector 48 takes when the sensor 10 detects the OFF state, and point d3 the position the detector 48 takes upon lapse of the predetermined time after the sensor 10 has detected the OFF state. As is evident from the broken line, the detector 48 does not start near motion to the subject 50a the moment the sensor 10 detects the OFF state. Rather, the detector 48 continues to far motion from the subject 50a until the predetermined time has expired. Thus, the detector 48 does not repeat a short near motion and a short far motion, making an unnecessary zig-zag motion, generally known as "inching motion."

When the detector 48 reaches the scanning termination position represented by the data input from the console, it is stopped from scanning the subject 50a.

As described above, the detector 48 continues to far motion from the subject 50a up to the expiration of the predetermined time, and thus makes no inching motion whatever. Another, more efficient method of preventing an inching motion, which can be used if the sensor 10 is of the type shown in FIGS. 8A to 8C or the type shown in FIGS. 9A to 9C, will be described with reference to the flow chart of FIG. 24. In the following description, it will be assumed that the sensor 10 comprises the counter-type optical sensors illustrated in FIGS. 9A to 9C.

Figure 22:
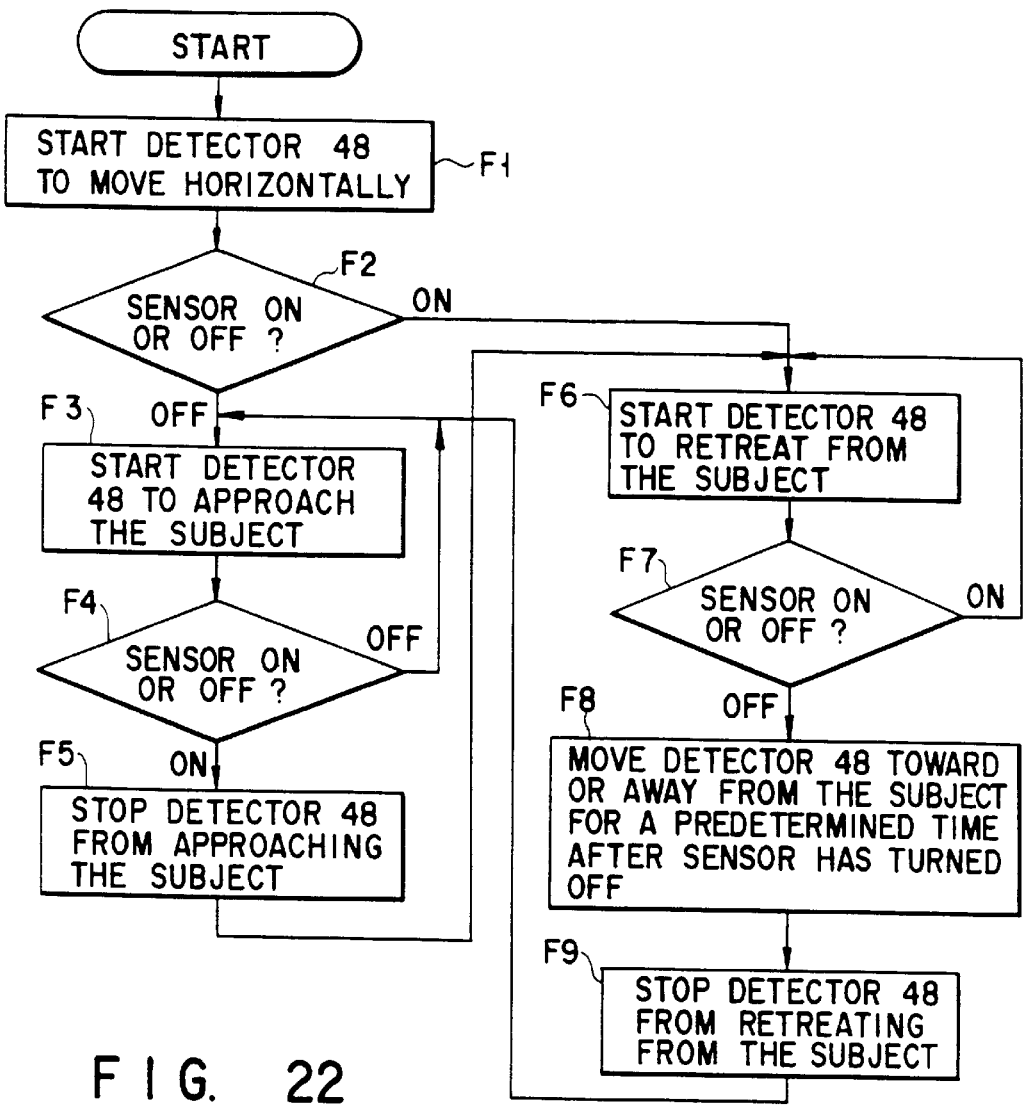
FIG. 22 is a flow chart for explaining how the detector of a scintillation camera, according to the invention, performs a scanning operation while being moved in a horizontal direction, in order to acquire data from a subject.

This method is similar to the method illustrated in FIG. 22. It is characterized in that the flow does not immediately go to Step F3 when at least one of the light-receiving elements 12 changes from the ON state to the OFF state in Step F7. In other words, the detector 48 does not approach the subject 50a until a specific condition holds in Step F10. In Step F10 it is determined whether a predetermined time has elapsed from the time any one of the light-receiving elements 12 changes from the ON state to the OFF state or whether the detector 48 has moved a distance L from the point at which where the element 12 changes from the ON state to the OFF state.

Figures 24, 25:
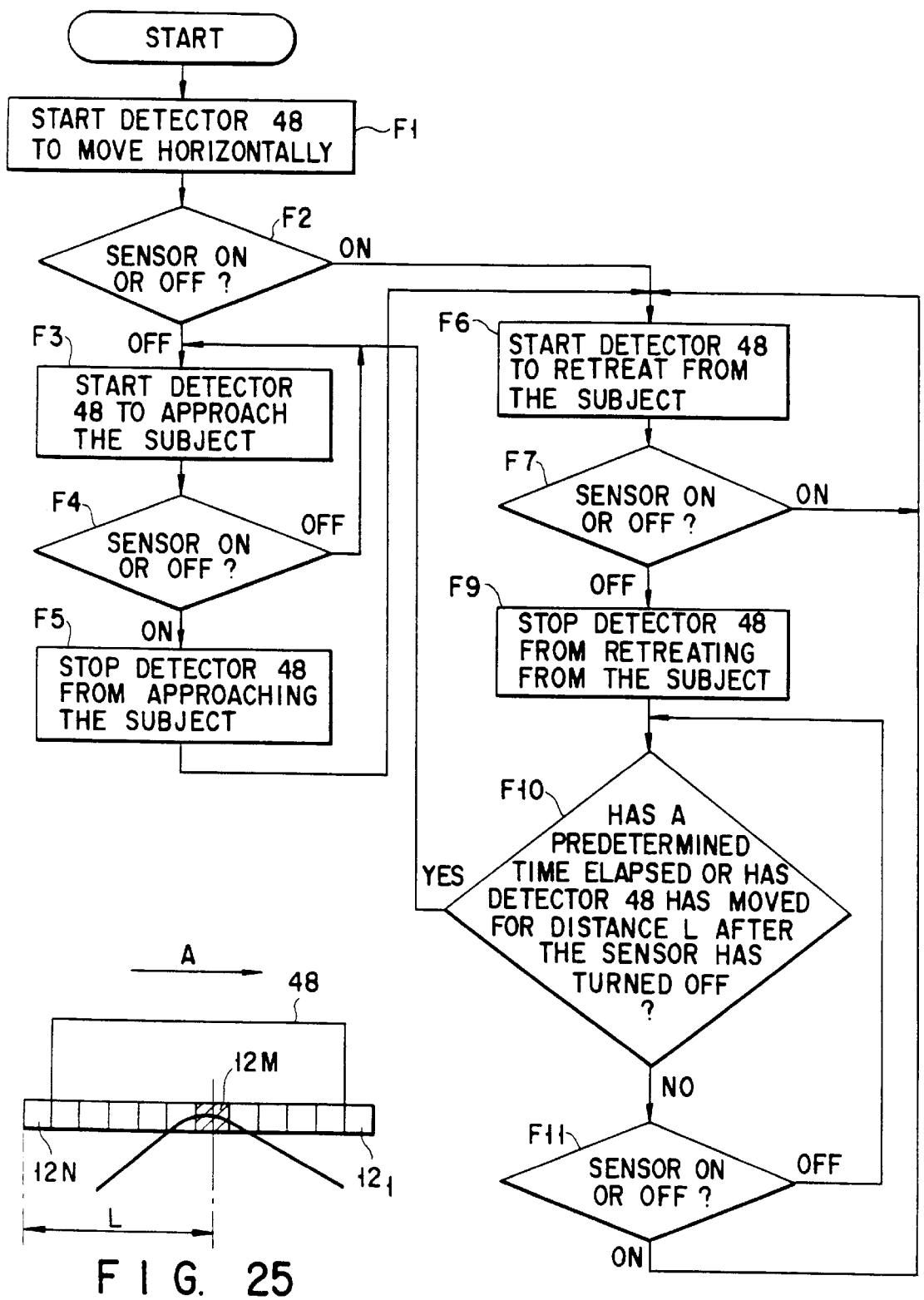
FIG. 24 is a flow chart for explaining how the detector of the scintillation camera performs a scanning operation without making an inching motion.
FIG. 25 is a diagram for explaining the distance L, a condition necessary for starting the approach of the detector in the scanning operation illustrated in FIG. 24.

With reference to FIG. 25, the distance L will be described. In FIG. 25, arrows A' indicates the direction in which the detector 48 is moved horizontally. Assume that the detector 48 is moved along the subject 50a, from head to toe, in order to acquire data from the subject 50a. When the detection surface of the detector 48 approaches a predetermined distance from the subject 50a, or some of the light-receiving elements 12 change from the OFF state to the ON state. The distance between the foremost one of the elements 12 which undergo this state change and the rearmost light-receiving element $12_N$ is the distance L. The distance L can be obtained at the time of designing the sensor 10 once the intervals at which the elements 12 are located are set. The distance L is stored in a memory (not shown) incorporated in the frame control circuit 30 and is read therefrom whenever necessary and used in Step F10.

Since the detector 48 does not approach the subject 50a after the detector 48 has detects the OFF state (Step f7) until the predetermined time has elapsed or the detector 48 has moved the distance L, the detector 48 is prevented from making an inching motion. That is, the detector 48 continues to move horizontally until the predetermined time has elapsed or the detector 48 has moved the distance L, while not approaching the subject 50a. When it is determined in Step F11 that the sensor 10 has changed from the OFF state to the ON state, the flow returns to Step F6, in which the detector 48 is started on a far motion from the subject 50a.

In the three embodiments described above, the detector remains at a predetermined distance away from the subject 50a throughout the data acquisition. A fourth embodiment of the invention will be described, in which the sensor detects the presence or absence of a subject 50a on the bed 50b, the detectors automatically start and end the scanning at proper times, and the whole-body scanning length is calculated.

Figure 26A:
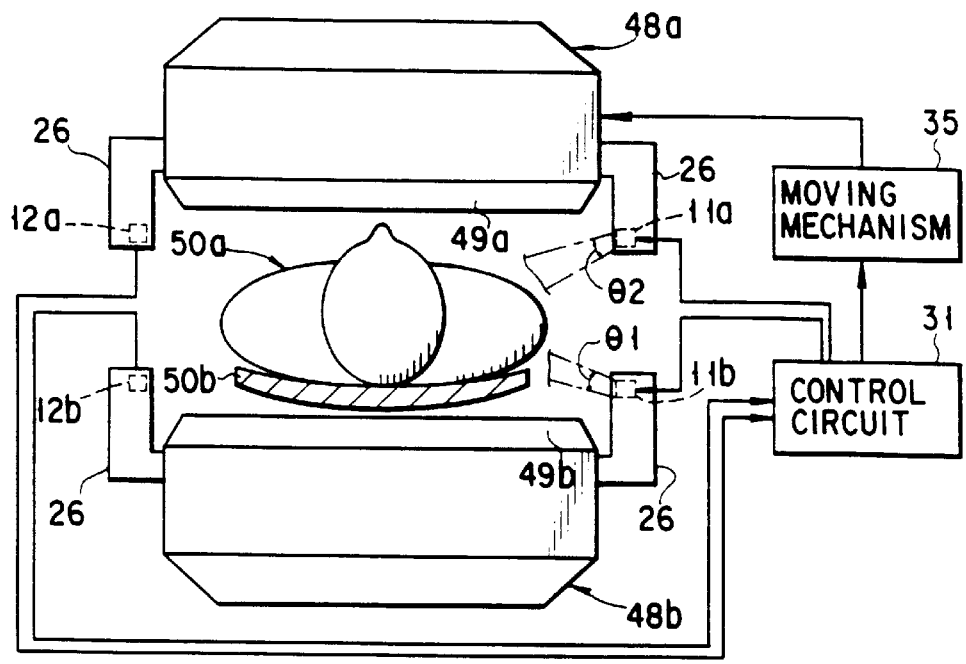
FIGS. 26A and 26B are a front view and a side view, respectively, of a scintillation camera according to a fourth embodiment of present invention.
Figure 26B:
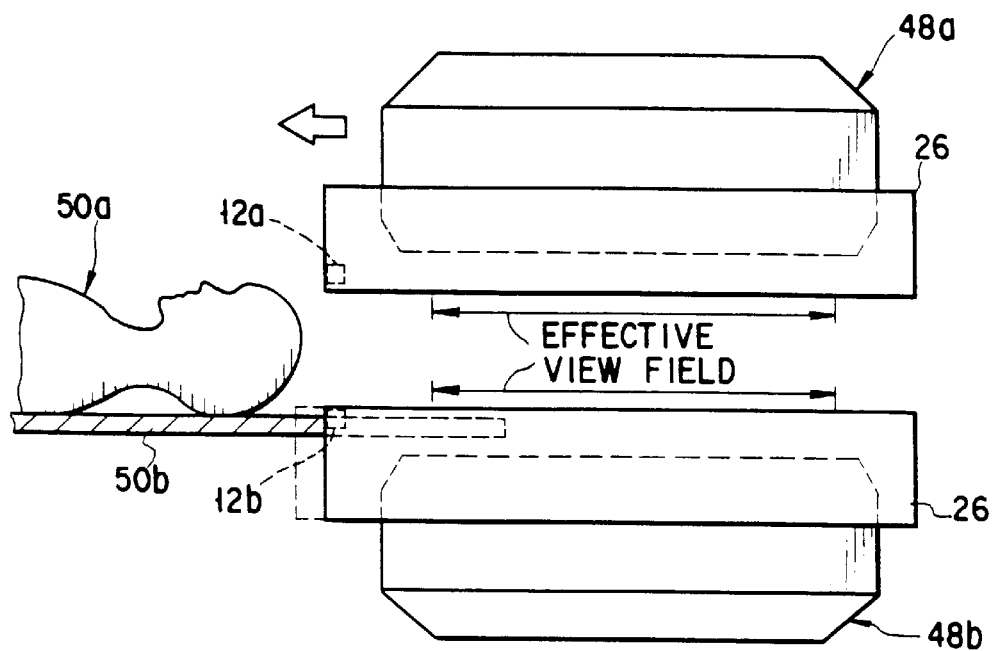

FIGS. 26A and 26B are a front view and a side view, respectively, of the scintillation camera according to the fourth embodiment of the present invention. The components of this camera, which are similar or identical to those shown in FIGS. 11 and 12 are designated by the same numerals in FIGS. 26A and 26B and will not be described in detail.

The scintillation camera shown in FIGS. 26A and 26B differs in two respects from the first to third embodiments. First, two detectors 48a and 48b are so located that their respective collimators 49a and 49b oppose, with a bed 50a interposed between them. Second, the detectors 48a and 48b are moved together in substantially the same manner by means of a drive mechanism 35.

The scintillation camera has two optical sensors for detecting whether a subject lies on the bed 50b or not. The first optical sensor comprises a light-emitting elements lia and a light receiving element 12b, and the second optical sensor comprises a light-emitting element 11b and a light-receiving element 12a. The elements 11a and 12a are held by a sensor holder 26 attached to the detector 48a. Similarly, the elements 11b and 12b are held by a sensor holder 26 secured to the detector 48b.

The elements 11a and 12b of the first sensor are positioned such that the element 12b can receive the light from the element 11a when no subject lies on the bed 50b, and cannot receive the light when a subject 50a lies on the bed 50b. Also, elements 11b and 12a of the second sensor are positioned such that the element 12a can receive the light from the element 11b when no subject lies on the bed 50b and cannot receive the light when a subject 50a lies on the bed 50b. The light-emitting elements 11a and 11b emit light beams which diverge at angles θ1 and θ2, respectively, so that both sensors may detect the absence or presence of a subject on the bed 50b with high reliability, regardless of the body thickness of the subject.

As shown in FIG. 26, the scintillation camera further comprises a control circuit 31 for controlling the drive mechanism 35 in accordance with the detection signals supplied from the light-receiving elements 12a and 12b.

The operation of the fourth embodiment of the invention will now be described, with reference to FIG. 27 and FIGS. 28A and 28B. FIG. 27 is a flow chart explaining the operation of the embodiment. FIG. 28A explains how the camera of FIGS. 26A and 26B operates when a subject 50a lies on the bed 50b. FIG. 28B explains how the camera of FIGS. 26A and 26B operates when no subject lies on the bed 50b.

First, as shown in FIG. 27, a subject 50a lies on the bed 50b in Step G1. Next, in Step G2, the detectors 48a and 48b are moved away from each other, and the whole rotation angle is automatically set to 0°/180°, whereby both detectors are rotated to their initial positions from the positions they take upon completion of the previous scanning. In Step G3, the detectors 48a and 48b are moved horizontally in the direction of the arrow shown in FIG. 26B, while operating the light-emitting elements hla and 11a and the light-receiving elements 12a and 12b.

When the detectors 48a and 48b are at the positions shown in FIG. 26B, the light beams emitted from the elements 11a and 11b reach the light-receiving elements 12b and 12a, respectively. The light-receiving element 12a generates a signal which indicates that no part of a subject 50a exists between the elements 11b and 12a, and the light-receiving element 12b generates a signal which indicates that no part of the subject 50a exists between the elements 11a and 12b. These signals are supplied to the control circuit 31. The magnitudes of the signals decrease when the sensors moved to the vertex of the subject 30a, and the vertex interrupts the light beam emitted the light-emitting elements 11a and 11b.

In Step G4, the control circuit 31 determines whether or not the sensors have detected the vertex of a subject 50a, more precisely whether or not the magnitudes of the signals from the light-receiving elements 12a and 12b have decreased. If No, Steps G3 and G4 are repeated, whereby the circuit 31 controls the drive mechanism 35 such that the mechanism 35 continues to move the detectors 48 and 48b horizontally in the direction or the arrow (FIG. 26B). If Yes, in Step G4, that is, if the sensors have been moved to the vertex of the subject 30a, the flow goes to Step G5.

In Step S5, the control circuit 31 causes the drive mechanism 35 to move the detectors 48a and 48b further until the right edge of the effective view field (FIG. 26B) common to both detectors reaches the vertex of the subject 50a. More specifically, data representing the distance between the right edge of the effective view field and the elements 11a, 11b, 12a and 12b, as measured in the horizontal direction, is stored in a memory connected to the control circuit 31, and the circuit 31 controls the drive mechanism 35 in accordance with this data, whereby the mechanism 35 moves the detectors 48a and 48b for said distance.

Then, in Step G6, the detectors 48a and 48b perform so-called "window opening," starting to acquire data from the subject 50a.

In Step G7, the control circuit 31 controls the drive mechanism 35 such that the detectors 48a and 48b are moved horizontally in predetermined paths, while maintaining the elements 11a, 11b, 12a and 12b in operative condition. As a result of this, both detectors 48a and 48b continue to acquire data from the subject 50a. It is desirable that the paths of the detectors 48a and 48b be as close to the subject 50a as possible so that the detectors 48a and 48b may acquire reliable data.

Thereafter, in Step 8, the control circuit 31 determines whether or not the sensors (i.e., the elements 11a, 11b, 12a and 12b) have detected the toes of the subject 30a, from the signals supplied from the sensors.

If No in Step 8, that is, if the sensors have not moved beyond the toes of the subject 50a and the magnitudes of the signals from the light-receiving elements 12a and 12b therefore have not increased yet, Steps C7 and G8 are repeated, whereby the circuit 31 controls the drive mechanism 35 such that the mechanism 35 continues to move the detectors 48 and 48b in the direction or the arrow (FIG. 26B) until the sensors are moved beyond the toes of the subject 30a. If Yes in Step G8, that is, if the sensors have been moved a little beyond the foot-tips of the subject 30a, the flow goes to Step G9.

In Step S9, the control circuit 31 causes the drive mechanism 35 to move the detectors 48a and 48b further until the right edge of the effective view field (FIG. 26B) reaches the toes of the subject 50a. More specifically, data representing the distance between the left edge of the effective view field and the elements 11a, 11b, 12a and 12b, as measured in the horizontal direction, is stored in a memory connected to the control circuit 31, and the circuit 31 controls the mechanism 35 in accordance with this data, whereby the mechanism 35 moves the detectors 48a and 48b for said distance.

Next, in Step G10, the detectors 48a and 48b perform so-called "window closing," thus terminating the data acquisition from the subject 50a.

Finally, in Step G11, the control circuit 31 calculates the height of the subject 50a from the period between the time of detecting the vertex and the time of detecting the toes, and out-puts the height, thus calculated, as the whole-body scanning length. The whole-body scanning length is displayed on a monitor (not shown).

As described above, both detectors 48a and 48b can be automatically located at a scanning start position in the fourth embodiment, in preparation for the acquisition of whole-body data from a subject 50a. Hence, it is easy for an operator to operate the scintillation camera according to the fourth embodiment of the present invention.

In addition, the scanning termination position is automatically detected, and the detectors 48a and 48b are automatically stopped at the scanning termination position. Hence, it is unnecessary for the operator to measure the height of the subject 50*a* and input the height as the whole-body scanning length. Automatically measured, the whole-body scanning length is, in most cases, more accurate than the length the operator may measure. This would help to achieve optimal display of the whole body of the subject 50*a*.

Optical sensors, which may be used as in the sensor or sensors, used in combination with the first to fourth embodiments described above, will now be described.

FIG. 29 shows a first example of the optical sensor 10 used in the present invention. As shown in FIG. 29, the sensor comprises light-emitting elements 11 and light-receiving elements 11. The elements 11 are arranged on the substrate 22 of a light-emission control circuit substrate 22, and the elements 12 on the substrate 24 of a light-reception control circuit. The elements 11 and the elements 12 are located in the same plane. Each light-receiving element 12 opposes the associated light-emitting element 11 and can, therefore, detect any object located between it and the associated light-emitting element 11.

A pair of slit units arranged between the array of light-emitting elements 11 and that of light-receiving elements 12, extending along these arrays, respectively. They are provided to prevent the light emitted from each element 11 from scattering and to prevent the light reflected from any object between the arrays of elements 11 and 12 from entering any light-receiving element 12. Each slit unit comprises a slit structure 16 and a frame 17 holding the slit structure 16. It would suffice to use only one slit unit extending along either the array of light-emitting element 11 or the array of light-receiving elements 12. Furthermore, the slit units may be replaced by plates each having a number of through holes or by units each comprising parallel thin plates spaced apart by spacers.

As shown in FIG. 30, the slit structure 16 of each slit unit is a honeycomb structure made of aluminum foil having a thickness of about 0.04 mm. Each cell of the honeycomb structure, which defines a slit, has a depth of about 15 mm and an inter-face width of about 5 mm. The thickness of the foil and the inter-face width of the cell can be varied if necessary. The depth of the cell may range from about 5 mm to 30 mm, preferably 10 mm to 20 mm. If the cell depth is too small, the slit unit will fail to prevent the light emitted from each element 11 from scattering or the light reflected from any object between the arrays of elements 11 and 12 from reaching any light-receiving element 12. If the cell depth is too large, the sensor 10 will be too large.

A method of manufacturing either slit unit will be described, with reference to FIGS. 31A to 31E.

Figure 31A:
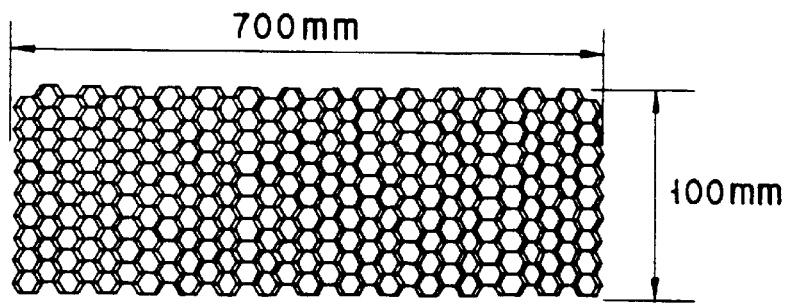
FIGS. 31A to 31E are diagrams for explaining a method of manufacturing the slit unit.
Figure 31B:
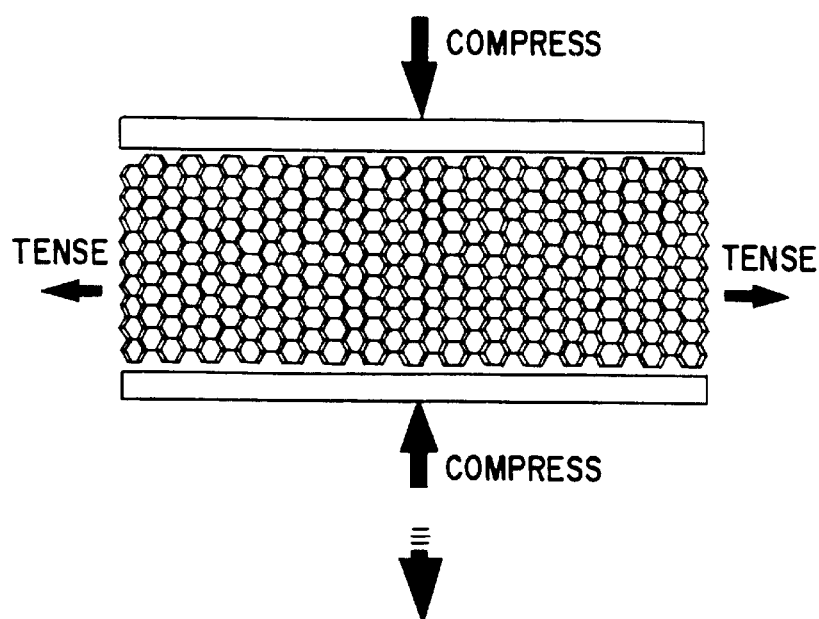
Figure 31C:
Figure 31D:
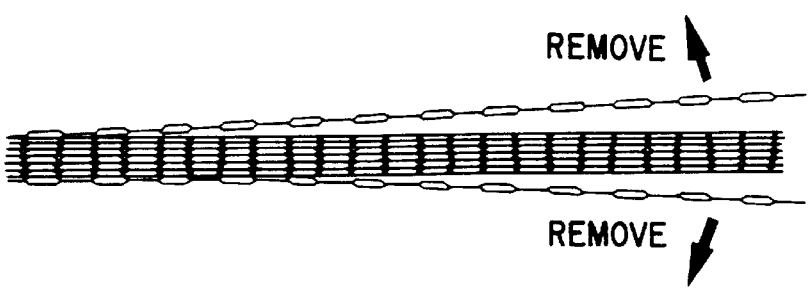
Figure 31E:
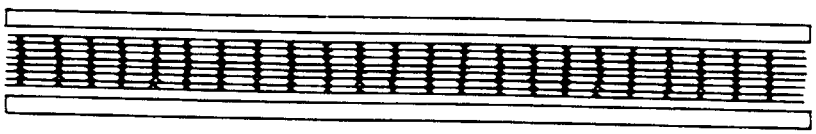

First, as shown in FIG. 31A, a honeycomb structure made of aluminum foil, 700 mm long and 100 mm high, composed of cells about 15 mm deep. The structure is coated with mat black paint or the like, so as not to reflect or scatter light. Next, as shown in FIG. 31B, the honeycomb structure is compressed between two flat plates, while being pulled at both ends. Unless the structure is pulled, the cells will not be compressed uniformly in some case. As a result, a compressed structure shown in FIG. 31C is obtained. Then, cell layers are peeled off as shown in FIG. 31C, thereby reducing the number of cell layers to a desired value. Finally, as shown in FIG. 31D, the compressed honeycomb structure is pulled into the gap between two parallel plates, while being pulled at both ends. The resultant structure is cut at both ends, forming a slit unit which has a desired length.

Figure 32:
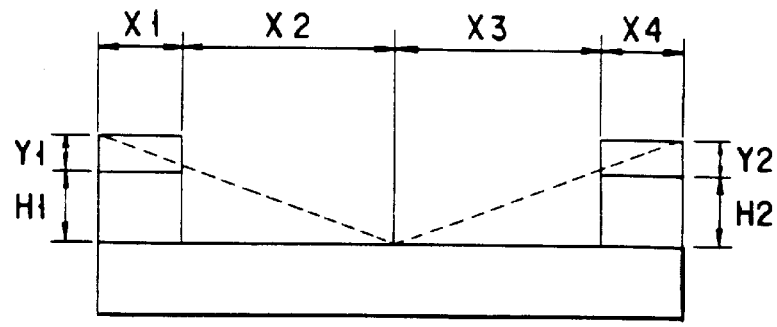
FIG. 32 is a diagram for explaining the effect resulting from the use of the slit units manufactured by the method shown in FIGS. 31A to 31E.

As is shown in FIG. 32, the two identical slit structures 16 having distance H1 and H2 between the object and the sensor, and depths X1 and X4 are spaced apart for a distance (X2+X3). On the basis of these dimensional values H1, H2, X1, and X2, slit diameters Y1 and Y2 (i.e., inter-face widths) are determined for the slit structures 16, respectively. The depths X1 and X4 and the slit diameters Y1 and Y2 can be set at any values desirable. The number of cell layers forming each slit structure 16 can be varied. In addition, the slit structure 16 can easily be coated with mat paint.

Figure 33A:
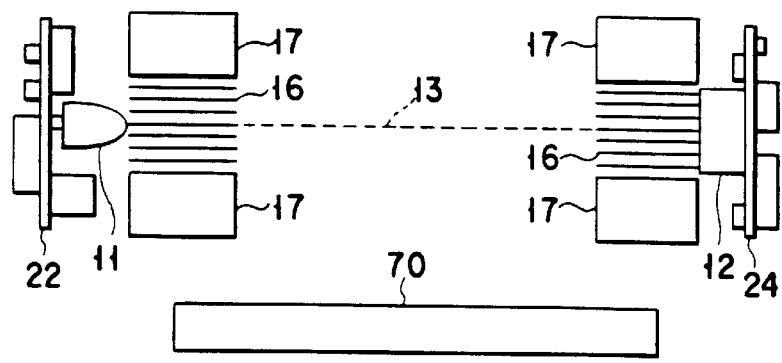
FIGS. 33A and 33B are diagrams showing a second example of the sensor.
Figure 33B:
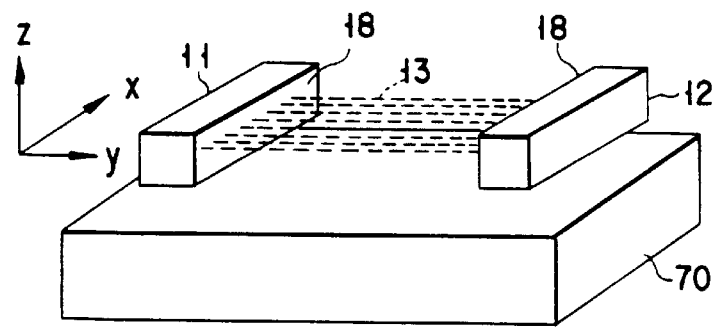

A second example of the sensor 10 will be described, with reference to FIGS. 33A and 33B. FIGS. 33A and 33B are a sectional view and a perspective view, respectively, both schematically showing the sensor.

As shown in FIG. 33A, this sensor comprises light-emitting elements 11 for emitting near infrared beams having a wavelength of 940 nm and light-receiving elements 12 for receiving the near infrared beams. The elements 11 are arranged on the substrate 22 of a light-emission control circuit substrate 22, and the elements 12 on the substrate 24 of a light-reception control circuit. The elements 11 are spaced apart from one another at intervals of 10 mm. Similarly, the elements 12 are spaced apart from one another at intervals of 10 mm. Each light-receiving element 12 opposes the associated light-emitting element 11, spaced apart therefrom for a distance of 800 mm, for detecting any object located between it and the associated light-emitting element 11. The sensor further comprises two slit units of the type shown in FIG. 29. The slit units are arranged between the array of light-emitting elements 11 and that of light-receiving elements 12, extending along these arrays, respectively. They prevent the light emitted from elements 11 from scattering to a reflector 70 extending along them and prevent the light reflected by the reflector 70 from reaching the light-receiving element 12.

As shown in FIG. 33B, an array composed of n light-emitting elements 11 extends along the X axis, and an array composed of n light-receiving elements 12 extends parallel to the array of elements 11 such that the elements 12 oppose the elements 11, respectively. Two slit units 18, each comprising a slit structure 16 and a frame 17, are arranged in front of these arrays, respectively. The n optical axes, each extending between one light-emitting element 11 and the associated light-receiving element 12, lie in an X-Y plane, extending parallel along the Y axis. The reflector 70 lies in a plane parallel to the X-Y plane, as well. Hence, the sensor can detect any object existing in the X-Y plane or moving thereto.

Since the slit units 18, each having a honeycomb structure, can easily be manufactured by the method explained with reference to FIGS. 31A to 31E, it is easy to manufacture the second example of the sensor 10.

FIG. 34 is a diagram illustrating a third example of the sensor 10. This sensor comprises an array of light-emitting elements 11 and an array of light-emitting elements 12. The array of elements 11 is mounted on a light emission control circuit board 22, and the array of elements 12 on a light reception control circuit board 24. These arrays are spaced apart by 800 mm, extending parallel to each other and to the plane of the drawing. The light-emitting elements 11 are arranged at intervals of 15 mm, for emitting near infrared beams having a wavelength of 940 nm. The light-receiving elements 12 are arranged at intervals of 15 mm and oppose the light-emitting elements 11, respectively, for receiving the near infrared beams emitted from the associated elements 11. A honeycomb slit structure 16 is arranged in front of each light-emitting element 11, for preventing the near infrared beam emitted by the element 11 from scattering. Similarly, a honeycomb slit structure 16 is arranged in front of each light-receiving element 12, for preventing any light beam reflected or scattered from a reflector lying in a plane parallel to the plane of the drawing.

FIG. 35 shows a fourth example of the sensor 10. The fourth example has no honeycomb slit structures. Despite this, it can detect any object existing between an array of light-emitting elements $11_1$ to $11_N$ and an array of light-receiving elements $12_1$ to $12_N$, not influenced by light beams reflected or scattered from a reflector 70. As in the second example shown in FIG. 33B, the light-emitting elements $11_1$ to $11_N$ are arranged in an X-Y plane, spaced apart at regular intervals, and the light-receiving elements 12 are also arranged in the X-Y plane, spaced apart at regular intervals and opposing the light-emitting elements $11_1$ to $11_N$, respectively.

The fourth example of the sensor 10 operates in the following steps:

a. First, the light-emitting element $11_1$ emits beams, and the first two light-receiving elements $12_1$ and $12_2$ receive the beams as indicated by broken lines 81 in FIG. 35.

b. Then, the second light-emitting element $11_2$ emits beams, and the first three light-receiving elements $12_1$, $12_2$ and $12_3$ receive the beams as indicated by solid lines 82 in FIG. 35.

c. Next, the third light-emitting element $11_3$ emits beams, and the second, third and fourth light-receiving elements $12_2$, $12_3$ and $12_4$ receive the beams.

d. Further, any Mth light-emitting element (3<M<N) to emit beams, and said (M−1)th, Mth and (M+1)th light-receiving elements receive the beams; and e. Finally, the last light-emitting element $11_N$ emits beams, and the last two light-receiving elements $12_{N-1}$ and $12_N$ receive the beams.

The sequence of steps a to e is repeated at high speed. When at least one of the light-receiving elements $12_1$ to $12_N$ receives no beam at all, it is detected that an object exists between the array of light-emitting elements and the array of light-receiving elements. Since the two or three light-receiving elements can receive a beam emitted by one light-emitting element, substantially at the same time, an object which is smaller than the intervals at which the elements $11_1$ to $11_N$ and $12_1$ to $12_N$ are spaced apart. Needless to say, the fourth example of the sensor 10 may also have honeycomb slit structures as the second example shown in FIG. 33B.

Furthermore, the signals the light-receiving elements $12_1$ to $12_N$ generate as the sequence of steps a to e is repeated may be stored into a memory (not shown) and compared with the positions of the light-receiving elements which are known. In this case, the position of an object, if existing between the arrays of the light-emitting and -receiving elements, can be determined to the precision of the intervals at which the light-receiving elements $12_1$ to $12_N$ are spaced apart.

Moreover, it is possible to determine whether or not the light-emitting elements and the light-receiving elements are out of order. More specifically, the steps a to e are carried out with no object existing between the arrays of the elements $11_1$ to $11_N$ and $12_1$ to $12_N$, the signals $Pon_1$ to $Pon_n$ which the light-receiving elements $12_1$ to $12_N$ generate in the process are stored into the memory. Then, the sequence of the following steps is performed, with no object existing between the arrays of the elements $11_1$ to $11_N$ and $12_1$ to $12_N$:

f. First, all light-emitting elements, except the element $11_1$, emit beams, and the signals $Poff_1$ generated by the light-receiving elements $12_1$ and $12_2$ are stored into the memory.

g. Next, all light-emitting elements, except the element $11_2$, emit beams, and the signals $Poff_2$ generated by the light-receiving elements $12_1$, $12_2$ and $12_3$ are stored into the memory.

h. Then, all light-emitting elements, except the element $11_3$, emit beams, and the signals $Poff_3$ generated by the light-receiving elements $12_2$, $12_3$ and $12_4$ are stored into the memory.

i. Further, all light-emitting elements, except any Mth light-emitting element (3<M<N) emit beams, and the signals $Poff_4$ generated by the elements $12_3$, $12_4$ and $12_5$, the signals $Poff_m$ generated by the elements $12_{M-1}$, $12_M$ and $12_{M+1}$, are stored into the memory.

j. Finally, all light-emitting elements, but the element $11_N$, emit beams, and the signals $Poff_n$ generated by the light-receiving elements $12_{N-1}$ and $12_N$ are stored into the memory.

If the signals $Pon_1$ to $Pon_n$ indicate absence of an object, and the signals $Poff_1$ to $Poff_n$ also indicate absence of an object, it is determined that all light-emitting elements and all light-receiving elements operate well.

If the signals $Pon_1$ to $Pon_n$ indicate absence of an object, while the signals $Poff_m$ (1<m<n) indicate presence of an object, it is determined that the light-receiving element $12_M$ (1<M<N) cannot perform its function.

If the signals $Pon_m$ indicate presence of an object, while the signals $Poff_1$ to $Poff_n$ indicate absence of an object, it is determined that the light-emitting element $11_M$ cannot emit a beam.

If the signals $Pon_{m-1}$, $Pon_m$ and $Pon_{m+1}$ indicate presence of an object, while the signals $Poff_1$ to $Poff_n$ indicate absence of an object, it is determined that the light-receiving element $12_M$ cannot perform its function.

FIG. 36 illustrates a fifth example of the sensor 10. The fifth example has no honeycomb slit structures. Despite this, it can detect any object existing between an array of light-emitting elements $11_1$ to $11_N$ and an array of light-receiving elements $12_1$ to $12_N$, not influenced by light beams reflected or scattered from a reflector 70. As in the fourth example shown in FIG. 35, the fifth example comprises an array 71 of elements and an array 72 of elements, which are arranged in an X-Y plane, opposing each other, extending parallel to each other, and spaced apart from each other. The array 71 comprises two light-emitting elements $11_1$ and $11_2$ located at the ends of the array, respectively, and a plurality of light-receiving elements $12_1$ to $12_M$ arranged between the light-emitting elements $11_1$ and $11_2$. Similarly, the array 72 comprises two light-emitting elements $11_3$ and $11_4$ located at the ends of the array, respectively, and a plurality of light-receiving elements $12_1'$ to $12_M'$ arranged between the light-emitting elements $11_1$ and $11_2$.

The fifth example of the sensor 10 operates in the following steps:

a. First, the light-emitting element $11_1$ emits beams, and the light-receiving elements $12_1'$ to $12_M'$ simultaneously receive the beams as indicated by broken lines 83 in FIG. 36.

b. Then, the light-emitting element $11_2$ emits beams, and the light-receiving elements $12_1'$ to $12_M'$ simultaneously receive the beams as indicated by broken lines 84 in FIG. 36.

c. Next, the light-emitting element $11_3$ emits beams, and the light-receiving elements $12_1$ to $12_M$ simultaneously receive the beams as indicated by solid lines 85 in FIG. 36.

d. Further, the light-emitting element $11_4$ emits beams, and the light-receiving elements $12_1$ to $12_M$ simultaneously receive the beams as indicated by solid lines 86 in FIG. 36.

The sequence of steps a to d is repeated at high speed, whereby an object, if any between the arrays 71 and 72, can be detected. Since a plurality of light-receiving elements $12_1$ to $12_M$ or a plurality of light-emitting elements $12_1'$ to $12_{M'}$ receives beams at the same time, an object which is smaller than the intervals at which the light-receiving elements are spaced apart. It is desirable that the fifth example of the sensor 10 have honeycomb slit structures as the second example (FIG. 33B). If provided with honeycomb slit structures, the beams emitted from any light-emitting element can be directed at broader angles to the light-receiving elements. Needless to say, the fifth example of the sensor 10 can operate well if it has five or more light-emitting elements, instead of four, provided that at least one light-emitting member is located at each end of either array.

FIG. 37 shows a sixth example of the sensor 10. The sixth example has no honeycomb slit structures. Despite this, it can detect any object existing between an array of light-emitting elements $11_1$ to $11_N$ and an array of light-receiving elements $12_1$ to $12_N$, not influenced by light beams reflected or scattered from a reflector 70. As shown in FIG. 37, the sixth example comprises an array 73 of elements and an array 74 of elements, which are arranged in an X-Y plane, opposing each other, extending parallel to each other, and spaced apart from each other. The array 73 comprises two light-receiving elements $12_1$ and $12_2$ located at the ends of the array, respectively, and a plurality of light-emitting elements $11_1$ to $11_M$ arranged between the light-emitting elements $12_1$ and $12_2$. Similarly, the array 72 comprises two light-receiving elements $12_3$ and $12_4$ located at the ends of the array, respectively, and a plurality of light-emitting elements $11_1'$ to $11_M'$ arranged between the light-receiving elements $12_1$ and $12_2$.

The sixth example of the sensor 10 operates in the following steps:

a. First, the light-emitting elements $11_1$ to $11_M$ are sequentially operated, emitting beams toward the light-receiving element $12_3$, and the element $12_3$ receives these beams at the same time as indicated by the solid lines 88 in FIG. 37.

b. Next, the light-emitting elements $11_1$ to $11_M$ are sequentially operated again, emitting beams toward the light-receiving element $12_4$, and the element $12_4$ receives these beams at the same time as indicated by the solid lines 88 in FIG. 37.

C. Then, the light-emitting elements $11_1'$ to $11_M'$ are sequentially operated, emitting beams toward the light-receiving element $12_1$, and the element $12_1$ receives these beams at the same time as indicated by the broken lines 87 in FIG. 37.

d. Finally, the light-emitting elements $11_1'$ to $11_M'$ are sequentially operated again, emitting beams toward the light-receiving element $12_2$, and the element $12_2$ receives these beams at the same time as indicated by the broken lines 87 in FIG. 37.

The sequence of steps a to d is repeated at high speed, whereby an object, if any between the arrays 73 and 74, can be detected. Since a plurality of light-emitting elements $11_1$ to $11_M$ or a plurality of light-emitting elements $11_1'$ to $11_M'$ emit beams at the same time, an object which is smaller than the intervals at which the light-receiving elements are spaced apart. It is desirable that the sixth example of the sensor 10 have honeycomb slit structures as the second example (FIG. 33B). If provided with honeycomb slit structures, the beams emitted from any light-emitting element can be directed at broader angles to the light-receiving elements. Needless to say, the sixth example of the sensor 10 can operate well if it has five or more light-receiving elements, instead of four, provided that at least one light-receiving member is located at each end of either array.

Figure 38:
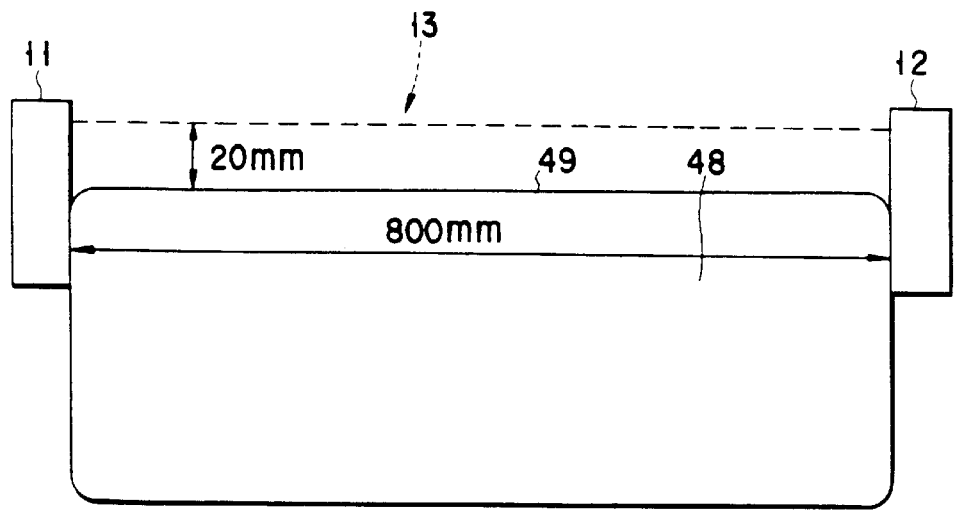
FIG. 38 is a diagram illustrating a scintillation camera having a sensor of the type shown in FIGS. 33A and 33B.

FIG. 38 illustrates a scintillation camera according to the present invention, which has a sensor of the type shown in FIGS. 33A and 33B.

As shown in FIG. 38, this scintillation camera further comprises a detector 48 having a detection surface 49 which is a reflector 70. The sensor comprises an array of n light-emitting elements 11 and an array of n light-receiving elements 12. These arrays are attached to the opposing sides of the detector 48. Although not shown in FIG. 38, two slit units 18, each comprising a slit structure 16 and a frame 17, are arranged in front of the arrays, respectively. The n light-emitting elements 11 oppose the n light-receiving elements 12, respectively, each for emitting a beam to the associated light-receiving element 12 along an optical axis 13. The elements 11 and the elements 12 protrude such that the n optical axes 13 lie in a horizontal plane 20 mm above the detection surface 49 of the detector 48. Hence, the sensor can detect any object at a distance equal to or less than 20 mm from the detection surface 49—not affected by light beams reflected or scattered from the reflector 70 (i.e., the detection surface 49 of the detector 48).

Thanks to the use of the non-contact type sensor, the detector 48 can be held at a predetermined distance from the body surface of a subject while being rotated in an orbit around the subject to acquire SPECT data therefrom. Also the detector 48 can be moved along the ridge line of the subject in order to acquire data required for forming a whole-body image of the subject. Thus, it is unnecessary to store in a memory the data representing the desired orbit or the data representing the desired orbit is not stored in the memory. The time for acquiring the SPECT data from a subject can be shorter than otherwise, whereby the throughput increases and the operator's toil is lessened, and the reliability of the scintillation camera is enhanced. Since the detector 48 can approach the bed and far therefrom, such that it remains always at a predetermined distance from the body surface of a subject, the image resolution of the camera is high. Two identical non-contact sensors of the type shown in FIG. 38 may be used, with a subject located between them, during the acquisition of the SPECT data, to thereby detect the body axis of the subject. This helps provide high-quality tomographic images of the subject.

The non-contact type sensor according to the present invention can be employed in combination with an x-ray diagnostic apparatus, instead of a scintillation camera used as a nuclear medicine diagnostic apparatus.

Some of the embodiments described above are designed to achieve whole-body data acquisition, whereas the other embodiments are designed to perform SPECT data acquisition. The present invention is not limited to these two types; it is applied to a scintillation camera which can perform both whole-body data acquisition and SPECT data acquisition, one after the other without a break. For instance, SPECT data acquisition may be started upon completion of whole-body data acquisition. In this case, the data showing a whole-body data acquisition start position and a SPECT data acquisition start position and the data specifying these types of data acquisition are input, and both types of data acquisition are started thereafter. Since the whole-body data acquisition and the SPECT data acquisition are sequentially effected in the order mentioned, without any break, the entire data acquisition time is shorter than otherwise.

Figure 39:
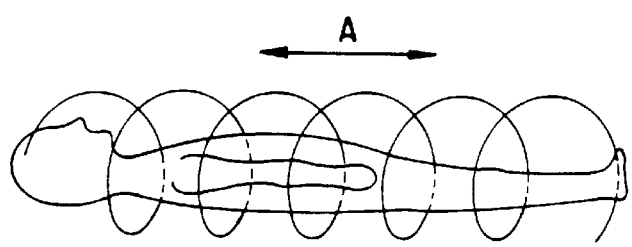
FIG. 39 is a diagram showing a path along which the detector of a scintillation camera according to the invention is moved to perform helical scanning.

In the embodiments of scintillation camera, described above, the detector 48 is horizontally moved, while remaining at the 0° position (FIG. 11), or is rotated around the subject, while not moving horizontally at all. According to the present invention, the detector 48 may be moved horizontally, while being rotated around the subject, as illustrated in FIG. 39. In this instance, the detector 48 is moved in a helical path, thus accomplishing so-called "helical scanning" to acquire SPECT from the subject.

In addition, the present invention can be applied to a scintillation camera comprising a plurality of detectors and a plurality of sensors, each of which can be housed within one sensor so that the sensor may be located close to any adjacent detector.

As described above, the detector is maintained at a predetermined distance from a subject throughout the whole-body data acquisition or the SPECT data acquisition. Instead, the detector may be moved along a prescribed whole-body data acquisition path or in a prescribed SPECT data acquisition orbit, and is made to far motion from the subject when it approaches the subject too much by near motion, and return to the prescribed path or orbit upon faring a predetermined distance from the subject or upon elapse of a predetermined period from the start of far motion.

In the above-described embodiments, the light-emitting and -receiving elements are located such that the optical axes they define lie in one plane. When any part of the subject interfere one or more of the optical axes, the detector 48 is made to far motion from the subject. Sometimes it is desirable that the detector 48 be located very near a part of the subject. On such an occasion, it suffices to render inoperative those of the light-emitting and -receiving elements which define optical axes to be interfered by said part of the subject.

Moreover, it is possible with the present invention to use a contact type sensor along with the non-contact type sensor. If this is the case, the contact type sensor serves to stop the detector 48 or move the same away from the subject the moment the detector 48 comes into contact with the subject. The use of both a contact type sensor and a non-contact type sensor can increase the safety of the scintillation camera. Further, a sensor, either a contact type one or a non-contact type one, may precede the detector 48 while moving together with the detector 48, thereby serving to prevent the detector 48 from contacting the subject. This also ensures safety.

In the embodiment described above, it is desirable that the light-emitting elements be infrared ray emitting ones, laser-beam emitting diodes, or the like.

Further, to achieve whole-body data acquisition, the subject may be scanned from the toe to the vertex, not vice versa as in some of the embodiments described above.

The above embodiments of the scintillation camera which has two detectors may be modified into one which has only one detector. In such a modification, it suffices to attach the sensor holders 26 to the opposing sides of the single detector, respectively, and to mount a light-emitting element 11 on the first holder 26 and a light-receiving element 12 on the second holder 26.

As shown in FIGS. 26A and 26B, the fourth embodiment has two sensor units each comprising a light-emitting element and a light-receiving element. Instead, a scintillation camera according to the invention may have only one sensor unit or three or more sensor units. Further, the sensor units may be connected to the rear ends of the sensor holders 26, instead of the forward ends thereof as shown in FIG. 25B.

In the above-described embodiments of the scintillation camera according to the invention, the bed is stationary, whereas the detector (or detectors) is movable. Alternatively, the bed may be movable and the detector is fixed in place.

Moreover, other various changes and modifications can be made, without departing from the scope and spirit of the present invention.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A scintillation camera comprising:
   detecting means having a surface and designed to acquire data from a subject by detecting radiation emitted from radioisotope administered to said subject;
   a sensor connected to a front portion of said detecting means and facing toward said subject for sensing a distance between said detecting means and a body surface of said subject for out-putting a signal representing the position of said subject; and
   holding means for holding said detecting means at a previously set distance from said body surface of said subject while said detecting means is acquiring the data;
   wherein said holding means changes a speed of toward and away movement on the basis of an output of said sensor.

2. The scintillation camera according to claim 1, wherein said holding means includes means for detecting absence or presence of the subject in a moving direction of said detecting means.

3. A scintillation camera according to claim 1, wherein said holding means further comprises a contact sensor for detecting a mutual contact of said detecting means and the subject.

4. A scintillation camera according to claim 1, further comprising:
   a sensor control means for detecting an ON state and an OFF state of said sensor;
   and wherein said holding means includes means for causing said detecting means to start approaching said subject after the detector means has retreated for a predetermined period or a first predetermined distance beginning from the time said detecting means retreats from said subject to a second predetermined distance therefrom after said sensor control means has detected an ON state.

5. A scintillation camera according to claim 1, further comprising:
   a sensor control means for detecting an ON state and an OFF state of said sensor;
   means for moving said detecting means in a prescribed path; and
   means for moving said detecting means from the prescribed path when said sensor control means detects an ON state while moving in the prescribed path and for moving said detecting means back to the prescribed path the moment said detecting means has moved for a predetermined time or a predetermined distance.

6. A scintillation camera according to claim 1, which further comprises data setting means for setting data representing a plurality of data acquisition methods and data representing a plurality of data acquisition start positions assigned to the methods, and in which said detecting means further comprises means for continuously acquiring data in accordance with data set by said data setting means.

7. A scintillation camera according to claim 1, wherein said sensor is an ultrasonic sensor for detecting the distance between the subject and said detecting means by using ultrasonic waves.

8. A scintillation camera according to claim 1, wherein said sensor is a reflection-type optical sensor for detecting the distance between the subject and said detecting means by emitting light to the subject and receiving the light reflected therefrom.

9. A scintillation camera according to claim 1, wherein said sensor is a tension sensor comprising a strip of cloth stretched in the same plane at a predetermined tension, for detecting the distance between said subject and said detecting means in accordance with changes in the tension.

10. A scintillation camera according to claim 1, wherein said sensor is a counter-type optical sensor comprising an array of light-emitting elements and an array of light-receiving elements opposing said array of light-emitting elements, respectively, for detecting the distance between said subject and said detecting means in accordance with signals which said array of light-receiving elements generate as said subject moves in a space between said array of light-emitting elements and said array of light-receiving elements.

11. A scintillation camera according to claim 1, further comprising means for housing said sensor when said sensor is out of use.

12. A scintillation camera according to claim 1, wherein said sensor includes:

a light-emitting element;

a light-receiving element opposing said light-emitting element, spaced apart therefrom by a predetermined distance, and located in the same plane as said light-emitting element; and a slit unit located in front of at least one of said light-emitting element and said light-receiving element.

13. A scintillation camera according to claim 12, wherein said slit unit is a honeycomb unit.

14. A scintillation camera according to claim 13, wherein said slit unit comprises a compressed honeycomb structure made of a thin plate and coated with dark mat paint, and a frame holding the compressed honeycomb structure.

15. A scintillation camera according to claim 1, wherein said sensor includes:

an array of light-emitting elements;

an array of light-receiving elements opposing said array of light-emitting elements, respectively, spaced apart therefrom by a predetermined distance, and located in the same plane as said array of light-emitting, elements;

a slit unit located in front of the elements of at least one of said array of light-emitting elements and said array of light-receiving elements; and means for preventing at least one element of said array of light-emitting elements from emitting a beam, and at least one element of said array of light-receiving elements from receiving a beam.

16. A scintillation camera according to claim 1, wherein said sensor includes:

an array of light-emitting elements for emitting beams;

an array of light-receiving elements opposing said array of light-emitting elements, spaced apart therefrom by a predetermined distance, and arranged in the same plane as said array of light-emitting elements, for receiving the beams emitted from said array of light-emitting elements; and means for applying the beam emitted from each light-emitting element sequentially to said light-receiving elements, repeatedly a number of times which is an integral multiple of the number of said light-emitting elements.

17. A scintillation camera according to claim 16, further comprising at least one honeycomb slit unit extending between said array of light-emitting elements and said array of light-receiving elements.

18. A scintillation camera according to claim 1, wherein said sensor includes:

two parallel arrays of light-emitting elements;

at least two light-receiving elements located at the ends of each of said arrays of light-emitting elements; and means for repeatedly applying the beams sequentially emitted from the light-emitting elements of one of said array to each of at least two light-receiving elements located at the ends of the other array.

19. A scintillation camera according to claim 18, further comprising at least one honeycomb slit unit extending between said two arrays of light-emitting elements.

20. A scintillation camera according to claim 1, wherein said sensor includes:

an array of first to Nth light-emitting elements;

an array of first to Nth light-receiving elements opposing said first to Nth light-emitting elements, respectively, spaced apart therefrom by a predetermined distance, and located in the same plane as said first to Nth light-emitting elements;

means for repeating the steps of;

causing the first light-emitting element to emit beams and the first and second light-receiving elements to receive the beams and generate signals;

causing the second light-emitting element to emit beams and the first, second and third light-receiving elements to receive the beams and generate signals;

causing any Mth light-emitting element (1<M<N) to emit beams and the (M−1)th, Mth and (M+1)th light-receiving elements to receive the beams and generate signals; and causing the Nth light-emitting element to emit beams and the (N−1)th and Nth light-receiving elements to receive the beams and generate signals; and means for recording the beams emitted by said first to Nth light-emitting elements and the signals generated by said first to Nth light-receiving elements, checking the beams and signals against the positions of said first to Nth light-emitting elements and the positions of said first to Nth light-receiving elements, thereby detecting a position of a subject existing between said array of first to Nth light-emitting elements and said array of first to Nth light-receiving elements.

21. A scintillation camera according to claim 1, wherein said sensor includes:

an array of first to Nth light-emitting elements;

an array of first to Nth light-receiving elements opposing said first to Nth light-emitting elements, respectively, spaced apart therefrom by a predetermined distance, and located in the same plane as said first to Nth light-emitting elements; and means for performing a first sequence of steps and a second sequence of steps when no object exists between said array of first to Nth light-emitting elements and said array of first to Nth light-receiving elements;

said first sequence of steps consisting of the steps of:

causing the first light-emitting element to emit beams and the first and second light-receiving elements to receive the beams and generate signals;

causing the second light-emitting element to emit beams and the first, second and third light-receiving elements to receive the beams and generate signals;

causing any Mth light-emitting element (1<M<N) to emit beams and the (M−1)th, Mth and (M+1)th light-receiving elements to receive the beams and generate signals; and causing the Nth light-emitting element to emit beams and the (N−1)th and Nth light-receiving elements to receive the beams and generate signals; and said second sequence of steps consisting of the steps of:

causing the first light-emitting element not to emit beams and the first and second light-receiving elements to generate signals;

causing the second light-emitting element not to emit beams and the first, second and third light-receiving elements to generate signals;

causing any Mth light-emitting element (1<M <N) not to emit beams and the (M−1)th, Mth and (M+1)th light-receiving elements to generate signals; and causing the Nth light-emitting element not to emit beams and the (N−1)th and Nth light-receiving elements to generate signals.

22. A scintillation camera according to claim 1, wherein said holding means changes a speed of toward and away movement according to area data corresponding to said output of said sensor, whereby said area data is used for measuring said distance between said detecting means and said body surface of said subject.

23. A scintillation camera according to claim 1, wherein said sensor is a tension sensor comprising a plurality of strings stretched in the same plane at a predetermined tension, for detecting the distance between said subject and said detecting means in accordance with changes in the tension.

* * * * *